US011957770B2

(12) United States Patent
Hoss

(10) Patent No.: US 11,957,770 B2
(45) Date of Patent: Apr. 16, 2024

(54) ORAL HYGIENE COMPOSITIONS AND METHODS OF USE

(71) Applicant: SMILE MAKERS, LLC, San Diego, CA (US)

(72) Inventor: Kami Hoss, San Diego, CA (US)

(73) Assignee: SMILE MAKERS, LLC, San Diego, CA (US)

( * ) Notice: Subject to any disclaimer, the term of this patent is extended or adjusted under 35 U.S.C. 154(b) by 0 days.

(21) Appl. No.: 17/746,817

(22) Filed: May 17, 2022

(65) Prior Publication Data

US 2023/0000739 A1 Jan. 5, 2023

Related U.S. Application Data

(60) Provisional application No. 63/311,383, filed on Feb. 17, 2022, provisional application No. 63/191,225, filed on May 20, 2021.

(51) Int. Cl.
| | | |
|---|---|---|
| A61K 8/24 | (2006.01) | |
| A61K 8/19 | (2006.01) | |
| A61K 8/21 | (2006.01) | |
| A61K 8/25 | (2006.01) | |
| A61K 8/34 | (2006.01) | |
| A61K 8/46 | (2006.01) | |
| A61K 8/67 | (2006.01) | |
| A61K 8/9789 | (2017.01) | |
| A61Q 11/00 | (2006.01) | |

(52) U.S. Cl.
CPC .......... *A61K 8/24* (2013.01); *A61K 8/19* (2013.01); *A61K 8/21* (2013.01); *A61K 8/25* (2013.01); *A61K 8/345* (2013.01); *A61K 8/466* (2013.01); *A61K 8/67* (2013.01); *A61K 8/676* (2013.01); *A61K 8/9789* (2017.08); *A61Q 11/00* (2013.01)

(58) Field of Classification Search
CPC ........... A61K 9/68; A61K 7/16; A61Q 11/00
USPC ..................................... 424/48, 49
See application file for complete search history.

(56) References Cited

U.S. PATENT DOCUMENTS

| 5,624,906 | A | * | 4/1997 | Vermeer | A61Q 11/00 |
| | | | | | 514/960 |
| 6,485,711 | B1 | * | 11/2002 | Olmstead | A61Q 11/00 |
| | | | | | 424/49 |
| 6,589,555 | B2 | | 7/2003 | Pandya | |
| 7,704,529 | B2 | | 4/2010 | Riman et al. | |
| 7,758,888 | B2 | | 7/2010 | Lapidot et al. | |
| 7,850,453 | B2 | | 12/2010 | Jodaikin et al. | |
| 7,959,902 | B1 | | 6/2011 | Postlewaite | |
| 7,998,219 | B2 | | 8/2011 | Riman et al. | |
| 8,168,161 | B2 | | 5/2012 | Scherl et al. | |
| 8,287,277 | B2 | | 10/2012 | Jodaikin et al. | |
| 8,287,842 | B2 | | 10/2012 | Katou et al. | |
| 8,367,043 | B2 | | 2/2013 | Gazzaniga et al. | |
| 8,449,918 | B2 | | 5/2013 | Lapidot et al. | |
| 8,518,383 | B2 | | 8/2013 | Haas | |
| 8,551,455 | B2 | | 10/2013 | Kristiansen et al. | |
| 8,647,606 | B1 | | 2/2014 | Postlewaite | |
| 8,715,625 | B1 | | 5/2014 | Rokitowski et al. | |
| 8,778,425 | B2 | | 7/2014 | Schechner et al. | |
| 8,944,819 | B2 | | 2/2015 | Faasse et al. | |
| 8,951,540 | B2 | | 2/2015 | Riman et al. | |
| 8,961,938 | B2 | | 2/2015 | Kato | |
| 9,034,301 | B2 | | 5/2015 | Sakuma et al. | |
| 9,066,889 | B2 | | 6/2015 | Golden | |
| 9,149,419 | B2 | | 10/2015 | Butler et al. | |
| 9,149,528 | B2 | | 10/2015 | McHale et al. | |
| 9,180,318 | B2 | | 11/2015 | Deng et al. | |
| 9,408,791 | B2 | | 8/2016 | Gualandi et al. | |
| 9,433,569 | B2 | | 9/2016 | Gualandi et al. | |
| 9,457,204 | B2 | | 10/2016 | Rau et al. | |
| 9,662,294 | B2 | | 5/2017 | Golden | |
| 9,744,108 | B2 | | 8/2017 | Dehghan et al. | |
| 9,877,929 | B2 | | 1/2018 | McHale et al. | |
| 10,022,318 | B2 | | 7/2018 | Rau et al. | |
| 10,039,698 | B2 | | 8/2018 | Itakura et al. | |
| 10,278,904 | B2 | | 5/2019 | Tsu et al. | |
| 10,307,357 | B2 | | 6/2019 | Stettler et al. | |
| 10,314,771 | B2 | | 6/2019 | Dehghan et al. | |
| 10,328,010 | B2 | | 6/2019 | Stettler et al. | |
| 10,426,725 | B2 | | 10/2019 | Cilurzo | |
| 10,588,833 | B2 | | 3/2020 | Baig et al. | |
| 10,596,076 | B2 | | 3/2020 | Donnet | |
| 10,695,370 | B2 | | 6/2020 | Reynolds | |

(Continued)

FOREIGN PATENT DOCUMENTS

| CN | 110934751 | 3/2020 | | |
| DE | 102019114401 | * 12/2020 | ........... | A61K 31/122 |

(Continued)

OTHER PUBLICATIONS

Choice-Dental-Browns-Plains, "Vitamin K2-The Miracle Vitamin for Good Teeth and Bones." https://www.choice-dental.com.au>vitamin-k2-the-miracle-vitamin-for-good-teeth-and-bones/. Published online Jan. 17, 2020. (Year: 2020).*

Boka, Take Back Your Mouth, 2 pages, dated Oct. 28, 2020, https://web. archive.org/web/20201028181529/https://www.boka.com/pages/our-science.

Business Insider, Connie Chen, I tried a $75 electric toothbrush with bristles made from activated charcoal—here's how it worked, 6 pages, dated Jan. 31, 2019, Boka Electric Toothbrush Review: It Cleans Effectively and Efficiently (businessinsider.com).

Revitin, REvitinA Prebiotic Toothpaste Ingredients, 3 pages, dated Oct. 5, 2019, https://web.archive.org/web/20191005051843/http://www.revitin.com/f/Revitin-Ingredients/.

(Continued)

*Primary Examiner* — Walter E Webb

(74) *Attorney, Agent, or Firm* — Knobbe, Martens, Olson & Bear, LLP

(57) ABSTRACT

Disclosed herein are oral hygiene compositions, dental flossing material, and methods of treatment using the same. In some embodiments, the oral hygiene composition comprises a remineralization agent, an anti-inflammatory agent, a prebiotic agent, and an alkalizing agent.

17 Claims, No Drawings

(56) References Cited

U.S. PATENT DOCUMENTS

| | | |
|---|---|---|
| 10,780,032 B1 | 9/2020 | Rajaiah et al. |
| 2003/0230319 A1 | 12/2003 | Marcon et al. |
| 2004/0170583 A1* | 9/2004 | Heeg ............... A61K 8/922 424/59 |
| 2012/0225053 A1 | 9/2012 | Dushenkov et al. |
| 2013/0164359 A1 | 6/2013 | Deng et al. |
| 2013/0272970 A1 | 10/2013 | Pimenta et al. |
| 2014/0079750 A1 | 3/2014 | Li et al. |
| 2015/0335557 A1* | 11/2015 | Bhushan ............. A61Q 11/00 424/57 |
| 2016/0324741 A1* | 11/2016 | Baig ............... A61K 8/8147 |
| 2016/0338924 A1 | 11/2016 | Stettler et al. |
| 2018/0133122 A1 | 5/2018 | Rajaiah et al. |
| 2019/0076343 A1 | 3/2019 | Curatola |
| 2019/0307657 A1 | 10/2019 | Wenk et al. |
| 2019/0336428 A1 | 11/2019 | Stettler et al. |
| 2019/0352719 A1 | 11/2019 | Shi et al. |
| 2019/0380929 A1 | 12/2019 | Sarikaya et al. |
| 2020/0054537 A1 | 2/2020 | Gottenbos |
| 2020/0060950 A1 | 2/2020 | Aoki et al. |
| 2020/0107997 A1 | 4/2020 | Donnet |
| 2020/0181026 A1 | 6/2020 | Kogai et al. |
| 2020/0246378 A1 | 8/2020 | Reynolds |
| 2020/0253854 A1 | 8/2020 | Moon et al. |
| 2020/0297019 A1 | 9/2020 | Stengel et al. |
| 2020/0337954 A1 | 10/2020 | Rajaiah et al. |
| 2020/0337955 A1 | 10/2020 | Rajaiah et al. |
| 2020/0345597 A1 | 11/2020 | Rajaiah et al. |
| 2020/0375857 A1 | 12/2020 | Rajaiah et al. |
| 2020/0376012 A1 | 12/2020 | Kim et al. |
| 2020/0390662 A1 | 12/2020 | Sagel |
| 2021/0007948 A1 | 1/2021 | Baig et al. |
| 2021/0022838 A1 | 1/2021 | Hashimoto |
| 2021/0069096 A1 | 3/2021 | DeBaun |
| 2021/0093525 A1 | 4/2021 | Baig et al. |

FOREIGN PATENT DOCUMENTS

| | | | | |
|---|---|---|---|---|
| JP | 2004250374 | * | 9/2004 | ............... A61K 7/16 |
| WO | WO 2021/023695 | | 2/2012 | |
| WO | WO2012/100991 | * | 8/2012 | ............ A61K 35/74 |
| WO | WO 2015/000082 | | 1/2015 | |
| WO | WO2015074241 | * | 5/2015 | ................ C07F 9/09 |
| WO | WO 2019/226921 | | 11/2019 | |
| WO | WO 2020/099068 | | 5/2020 | |
| WO | WO 2020/140706 | | 7/2020 | |
| WO | WO 2020/141201 | | 7/2020 | |
| WO | WO 2020/212131 | | 10/2020 | |
| WO | WO 2020/219319 | | 10/2020 | |
| WO | WO 2020/219320 | | 10/2020 | |
| WO | WO 2020/219321 | | 10/2020 | |
| WO | WO 2020/219322 | | 10/2020 | |
| WO | WO 2020/234609 | | 11/2020 | |
| WO | WO 2020/252500 | | 12/2020 | |
| WO | WO 2021/007196 | | 1/2021 | |
| WO | WO 2021/046047 | | 3/2021 | |

OTHER PUBLICATIONS

Tom's of Maine Toothpaste, Explore Our Ingredients, 4 pages, dated Aug. 1, 2020, https://web.archive.org/web/20200801210522/https://www.tomsofmaine.com/our-promise/ingredients.

Carifree, Pro—CTx4 Gel 5000 1.1% Toothpaste, 3 pages, dated Sep. 30, 2020, https://web.archive.org/web/20200930181457/http://carif.com/product/ctx4-gel-5000/.

* cited by examiner

ORAL HYGIENE COMPOSITIONS AND METHODS OF USE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57, and Rules 4.18 and 20.6, including U.S. Provisional Application Nos. 63/191,225, filed May 20, 2021 and 63/311,383, filed Feb. 17, 2022.

BACKGROUND

Conventional oral care products contain fluoride as the primary active ingredient to protect enamel against cavities. However, overexposure to fluoride may cause detrimental effects, such as fluorosis and neurological toxicities. In addition, although oral care products may utilize hydroxyapatite in an attempt to strengthen teeth enamel, teeth have living structures on the inside and greater penetration of hydroxyapatite would be beneficial to help teeth remineralize from the outside and inside. Furthermore, conventional oral care products, including products that do and do not utilize fluoride, may contain ingredients that negatively affect oral microbiomes.

SUMMARY

For purposes of summarizing the disclosure and the advantages achieved over the prior art, certain objects and advantages of the disclosure are described herein. Not all such objects or advantages may be achieved in any particular embodiment. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments will become readily apparent to those skilled in the art from the following detailed description of the preferred embodiments having reference to the attached FIGURES, the invention not being limited to any particular preferred embodiment(s) disclosed.

In one aspect, an oral hygiene composition is described. The oral hygiene composition includes at least the following ingredients: a remineralization agent, an anti-inflammatory agent, a prebiotic agent, and an alkalizing agent.

In some embodiments, the remineralization agent comprises a compound selected from the group consisting of hydroxyapatite, vitamin D3, vitamin K2, calcium carbonate, dicalcium phosphate, fluoride, and combinations thereof. In some embodiments, the remineralization agent comprises hydroxyapatite, vitamin D3 and vitamin K2. In some embodiments, the oral hygiene composition includes: 1-20 wt. % hydroxyapatite, 0.00001-0.01 wt. % vitamin D3, and 0.00001-0.012 wt. % vitamin K2. In some embodiments, the composition further comprises fluoride. In further embodiments, the oral hygiene composition includes 0.01-0.5 wt. % fluoride. In further embodiments, the oral hygiene composition includes 0.01-1.5 wt. % fluoride.

In some embodiments, the anti-inflammatory agent comprises a compound or composition selected from the group consisting of methylsulfonylmethane, vitamin C, cranberry seed oil, sodium gluconate, and combinations thereof. In some embodiments, the anti-inflammatory agent comprises methylsulfonylmethane, vitamin C and cranberry seed oil. In some embodiments, the oral hygiene composition includes: 0.5-3 wt. % methylsulfonylmethane, 0.05-0.2 wt. % vitamin C, and 0.02-0.1 wt. % cranberry seed oil.

In some embodiments, the prebiotic agent comprises a compound or composition selected from the group consisting of inulin, xylitol, erythritol, cranberry seed oil, xanthan gum, *stevia* leaf extract, and combinations thereof. In some embodiments, the prebiotic agent comprises inulin, xylitol, and erythritol. In some embodiments, the oral hygiene composition includes: 3-7 wt. % inulin, 5-20 wt. % xylitol, and 5-10 wt. % erythritol. In some embodiments, the composition further comprises cranberry seed oil. In further embodiments, the oral hygiene composition includes 0.02-0.1 wt. % cranberry seed oil.

In some embodiments, the alkalizing agent comprises a compound selected from the group consisting of sodium bicarbonate, xylitol, erythritol, and combinations thereof. In some embodiments, the alkalizing agent comprises sodium bicarbonate, xylitol and erythritol. In some embodiments, the oral hygiene composition includes: 0.5-3.0 wt. % sodium bicarbonate, 5-20 wt. % xylitol and 5-10 wt. % erythritol.

In some embodiments, the composition further comprises a solvent. In some embodiments, the solvent comprises a compound selected from the group consisting of water, glycerin, and combinations thereof. In some embodiments, the solvent comprises water and glycerin. In some embodiments, the oral hygiene composition includes: 15-75 wt. % water and 1-20 wt. % glycerin.

In some embodiments, wherein composition further comprises a cleaning agent. In some embodiments, the cleaning agent comprises a compound or composition selected from the group consisting of hydrated silica, *Quillaja saponaria* extract, and combinations thereof. In some embodiments, the cleaning agent comprises hydrated silica and *Quillaja saponaria* extract. In some embodiments, the oral hygiene composition includes: 10-20 wt. % hydrated silica and 0.1-2 wt. % *Quillaja saponaria* extract.

In some embodiments, wherein composition further comprises a flavoring agent. In some embodiments, the flavoring agent comprises a compound or composition selected from the group consisting of xylitol, erythritol, *stevia*, peppermint flavor, spearmint flavor, strawberry flavor, vanilla flavor, chocolate flavor, cherry flavor, blueberry flavor, bubblegum flavor, grape flavor, apricot flavor, clove, ginger, wintergreen flavor, mango flavor, fennel, orange flavor, black currant flavor, watermelon flavor, cinnamon flavor, and combinations thereof.

In another aspect, a toothpaste composition is disclosed. The toothpaste composition includes:
 balance water;
 10-20 wt. % hydrated silica;
 1-20 wt. % hydroxyapatite;
 14-25 wt. % glycerin;
 5-15 wt. % erythritol;
 5-25 wt. % xylitol;
 1-10 wt. % inulin;
 0.5-3 wt. % methylsulfonylmethane;
 0.5-3 wt. % calcium carbonate;
 0.1-1 wt. % *Quillaja saponaria* extract;
 0.02-0.1 wt. % *stevia* leaf extract;
 0.2-1 wt. % dicalcium phosphate;
 0.01-1 wt. % xanthan gum;
 0.05-0.2 wt. % vitamin C;
 0.1-4 wt. % sodium gluconate;

0.02-0.1 wt. % cranberry seed oil;
0.001-0.002 wt. % vitamin D3;
0.004-0.008 wt. % vitamin K2;
0.1-2 wt. % color; and
0.1-0.5 wt. % flavoring agent.

In another aspect, the toothpaste composition includes:
balance water;
10-20 wt. % hydrated silica;
1-15 wt. % hydroxyapatite;
14-25 wt. % glycerin;
5-15 wt. % erythritol;
5-25 wt. % xylitol;
3-7 wt. % inulin;
0.5-3 wt. % methylsulfonylmethane;
0.1-1 wt. % *Quillaja saponaria* extract;
0.02-0.1 wt. % *stevia* leaf extract;
0.01-1 wt. % xanthan gum;
0.05-0.2 wt. % vitamin C;
0.1-4 wt. % sodium gluconate;
0.02-0.1 wt. % cranberry seed oil;
0.001-0.002 wt. % vitamin D3;
0.004-0.008 wt. % vitamin K2;
0.1-1.5 wt. % sodium fluoride;
0.1-2 wt. % color; and
0.1-0.5 wt. % flavoring agent.

In another aspect, a mouthwash composition is disclosed. The mouthwash composition includes:
balance water;
5-20 wt. % xylitol;
5-15 wt. % erythritol;
3-7 wt. % inulin;
0.5-20 wt. % hydroxyapatite;
1-5 wt. % glycerin;
0.1-3 wt. % sodium bicarbonate;
0.5-3 wt. % methylsulfonylmethane;
0.1-4 wt. % sodium gluconate;
0.05-0.5 wt. % vitamin C;
0.01-1 wt. % xanthan gum;
0.00001-0.00005 wt. % vitamin D3;
0.00001-0.0005 wt. % vitamin K2;
0.1-2 wt. % color; and
0.1-0.5 wt. % flavoring agent.

In another aspect, the mouthwash composition includes:
balance water;
5-20 wt. % xylitol;
5-15 wt. % erythritol;
3-7 wt. % inulin;
0.5-20 wt. % hydroxyapatite;
1-5 wt. % glycerin;
0.1-3 wt. % sodium bicarbonate;
0.5-3 wt. % methylsulfonylmethane;
0.1-4 wt. % sodium gluconate;
0.05-0.5 wt. % vitamin C;
0.01-1 wt. % xanthan gum;
0.01-0.5 wt. % sodium fluoride;
0.00001-0.00005 wt. % vitamin D3;
0.00001-0.0005 wt. % vitamin K2;
0.1-2 wt. % color; and
0.1-0.5 wt. % flavoring agent.

In another aspect, a mouth spray composition is disclosed. The mouth spray composition includes:
balance water;
5-20 wt. % xylitol;
5-20 wt. % erythritol;
3-7 wt. % inulin;
0.1-3 wt. % methylsulfonylmethane;
1-5 wt. % glycerin;
0.1-3 wt. % sodium bicarbonate;
0.1-4 wt. % sodium gluconate;
0.05-0.2 wt. % vitamin C;
0.01-1 wt. % xanthan gum; and
0.1-0.5 wt. % flavoring agent.

In another aspect, a dental floss device is disclosed. The dental floss device includes a flossing material and wherein the flossing material includes: a remineralization agent and a prebiotic agent.

In some embodiments, the remineralization agent comprises a compound selected from the group consisting of hydroxyapatite, vitamin D3, vitamin K2, fluoride, calcium carbonate, dicalcium phosphate, and combinations thereof. In some embodiments, the remineralization agent comprises hydroxyapatite. In some embodiments, the flossing material comprises 1-15 wt. % of hydroxyapatite. In some embodiments, the dental floss device further comprises vitamin D3 and vitamin K2. In further embodiments, the flossing material comprises 0.1-1 wt. % of vitamin D3 and 0.1-1 wt. % of vitamin K2. In some embodiments, the dental floss device further comprises fluoride. In further embodiments, the flossing material comprises 0.1-5 wt. % of fluoride. In some embodiments, the prebiotic agent comprises a compound or composition selected from the group consisting of inulin, xylitol, erythritol, cranberry seed oil, xanthan gum, *stevia* leaf extract, and combinations thereof. In some embodiments, the prebiotic agent comprises of xylitol, erythritol, and *stevia* leaf extract. In some embodiments, the flossing material includes: 1-15 wt. % of xylitol, 1-15 wt. % of erythritol, and 1-15 wt. % of *stevia* leaf extract. In some embodiments, the flossing material includes: 1-5 wt. % of hydroxyapatite, 0.5-3.5 wt. % of xylitol, 0.1-3 wt. % of erythritol, and 0.1-3 wt. % of *stevia* leaf extract.

In some embodiments, the flossing material further comprises a wax. In further embodiments, the wax comprises beeswax.

In another aspect, a method of treating a condition in a subject, preventing a condition in a subject or promoting oral hygiene in a subject, including administering the composition or device described herein to an oral cavity or tooth of the subject. In some embodiments, the subject is a child.

In some embodiments, the condition is a bone growth deficiency within a mouth or nose of the subject. In some embodiments, the condition is harmful bacterial growth within the oral cavity. In some embodiments, the promotion is beneficial bacterial growth within the oral cavity. In some embodiments, the condition is gingiva inflammation within the oral cavity. In some embodiments, the condition is tooth decay within the oral cavity. In some embodiments, the condition is a tooth mineralization deficiency. In some embodiments, the condition is a bone mineralization deficiency. In some embodiments, the condition is a gum disease and halitosis. In some embodiments, the promotion is teeth whitening. In some embodiments, the promotion is teeth buffering against acidic erosion. In some embodiments, the condition is tooth or root sensitivity.

In another aspect, a kit is described. The kit includes the composition or device described herein.

DETAILED DESCRIPTION

Oral hygiene compositions of the present disclosure may be used to prevent cavities, remineralize teeth from outside and inside, naturally whiten teeth, reduce tooth sensitivity, reduce tartar and calculus buildup, promote beneficial oral bacteria, and promote the long-term health of teeth and the mouth of an individual. The oral hygiene compositions of the present disclosure may also be used to treat or prevent gum disease and/or halitosis, balance oral or mouth pH, and protect teeth against acidic erosion. Moreover, such oral hygiene compositions may also aid in the development and growth of an individual's jaws and/or nasal septum. In some embodiments, the oral hygiene composition may include a remineralization agent or material, nutrients for teeth and bone growth and development, an anti-inflammatory agent or material, a prebiotic agent material, an alkalizing agent or material, or a mixture thereof.

Hydroxyapatite is a calcium mineral (e.g. calcium phosphate) that may help with remineralization of enamel, or the outside of teeth where enamel is present. However, within the teeth are living structures that require calcium to grow and defend against damage. For these interior structures of the teeth as well as the bones (e.g. jaw bones in the mouth/face and the nasal septum area), vitamin A, vitamin K (e.g. vitamin K2) and/or vitamin D (e.g. vitamin D3) may aid in the transfer of calcium to within the internal structures of the teeth, bone and/or nose. However, a large number of individuals are deficient in vitamin K (e.g. vitamin K2) and/or vitamin D (e.g. vitamin D3), and as such calcium deposition to teeth, bone and/or nose is limited even with additional calcium intake. As such, the oral hygiene compositions of the present disclosure allow remineralization of teeth and bones from the inside, and may further aid in the remineralization of teeth from the outside. This remineralization may also assist in healthy jawbone and nose grow, reduce the likelihood of dental crowding, and reduce the likelihood of nasal septum deviation.

As an example, in some embodiments, the oral hygiene composition includes:
a remineralization agent,
an anti-inflammatory agent,
a prebiotic agent, and
an alkalizing agent.

As another example, in some embodiments, the oral hygiene composition includes:
a remineralization agent,
an anti-inflammatory agent, and
a prebiotic agent.

As another example, in some embodiments, the oral hygiene composition includes:
an anti-inflammatory agent,
a prebiotic agent, and
an alkalizing agent.

As another example, in some embodiments, the oral hygiene composition includes:
a remineralization agent, and
a prebiotic agent.

Remineralization agents are generally used to whiten teeth, promote tooth translucency and glossiness, reduce sensitivity and pain, reduce risk of cavities, remineralize demineralized enamel, repair damage, remineralize dentin, and/or minimizes gum bleeding. Remineralization agents may include one or a grouping of nutrients necessary for teeth and bone growth and development. In some embodiments, the remineralization agent may be selected from hydroxyapatite, vitamin D (e.g., vitamin D3), vitamin K (e.g., vitamin K2), calcium carbonate, dicalcium phosphate, fluoride, or a mixture thereof. In some embodiments, the remineralization agent may comprise hydroxyapatite, vitamin D and vitamin K. In some embodiments, the remineralization agent may comprise hydroxyapatite and vitamin D. In some embodiments, the remineralization agent may comprise hydroxyapatite and vitamin K. In some embodiments, the remineralization agent may comprise hydroxyapatite. In some embodiments, the remineralization agent may comprise fluoride. In some embodiments, the remineralization agent may comprise fluoride and hydroxyapatite. In some embodiments, the remineralization agent may comprise fluoride and vitamin D. In some embodiments, the remineralization agent may comprise fluoride and vitamin K. In some embodiments, the remineralization agent may comprise fluoride, hydroxyapatite, vitamin D and vitamin K. In some embodiments, fluoride is sodium fluoride. In some embodiments, vitamin D is vitamin D3. In some embodiments, vitamin K is vitamin K2.

Hydroxyapatite may be utilized to assist tooth remineralization, tooth whitening, promote tooth translucency and glossiness, reduce tooth sensitivity and pain, reduce risk of cavities, promote growth and development of teeth from outside and inside, and bone, and/or minimize gum bleeding. In some embodiments, the composition comprises hydroxyapatite of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, 3 wt. %, 3.1 wt. %, 3.2 wt. %, 3.3 wt. %, 3.4 wt. %, 3.5 wt. %, 3.6 wt. %, 3.7 wt. %, 3.8 wt. %, 3.9 wt. %, 4 wt. %, 4.1 wt. %, 4.2 wt. %, 4.3 wt. %, 4.4 wt. %, 4.5 wt. %, 4.6 wt. %, 4.7 wt. %, 4.8 wt. %, 4.9 wt. %, 5 wt. %, 5.1 wt. %, 5.2 wt. %, 5.3 wt. %, 5.4 wt. %, 5.5 wt. %, 5.6 wt. %, 5.7 wt. %, 5.8 wt. %, 5.9 wt. %, 6 wt. %, 6.1 wt. %, 6.2 wt. %, 6.3 wt. %, 6.4 wt. %, 6.5 wt. %, 6.6 wt. %, 6.7 wt. %, 6.8 wt. %, 6.9 wt. %, 7 wt. %, 7.1 wt. %, 7.2 wt. %, 7.3 wt. %, 7.4 wt. %, 7.5 wt. %, 7.6 wt. %, 7.7 wt. %, 7.8 wt. %, 7.9 wt. %, 8 wt. %, 8.1 wt. %, 8.2 wt. %, 8.3 wt. %, 8.4 wt. %, 8.5 wt. %, 8.6 wt. %, 8.7 wt. %, 8.8 wt. %, 8.9 wt. %, 9 wt. %, 9.1 wt. %, 9.2 wt. %, 9.3 wt. %, 9.4 wt. %, 9.5 wt. %, 9.6 wt. %, 9.7 wt. %, 9.8 wt. %, 9.9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 31 wt. %, 32 wt. %, 33 wt. %, 34 wt. %, 35 wt. %, 36 wt. %, 37 wt. %, 38 wt. %, 39 wt. %, 40 wt. %, 41 wt. %, 42 wt. %, 43 wt. %, 44 wt. %, 45 wt. %, 46 wt. %, 47 wt. %, 48 wt. %, 49 wt. % or 50 wt. %, or any range of values therebetween. For example, in some embodiments, the amount of hydroxyapatite in the composition is or is about in any one of the following ranges: 1-20 wt. %, 5-15 wt. %, 4-16 wt. %, 3-17 wt. %, 2-18 wt. %, 1-19 wt. %, 2-4 wt. %, 0.1-1 wt. %, 0.1-5 wt. %, 1-5 wt. %, 5-10 wt. %, 1-10 wt. %, 10-15 wt. %, 1-15 wt. %, 10-20 wt. %, 20-30 wt. %, 30-40 wt. % or 40-50 wt. % (based on total weight of the composition). In some embodiments, the composition is free or substantially free of hydroxyapatite. In some embodiments, the hydroxyapatite particles are nano-hydroxyapatite. In some embodiments, the hydroxyapatite particles are micro-hydroxyapatite. In some embodiments, the hydroxyapatite has a $D_{50}$ particle size distribution of, or of about, 10 nm, 20 nm, 30 nm, 40 nm, 50 nm, 60 nm, 70 nm, 80 nm, 90 nm, 0.1 µm, 0.15 µm, 0.2 µm, 0.3 µm, 0.4 µm, 0.5 µm, 0.8 µm, 1 µm, 2 µm, 5 µm, 8 µm, 10 µm, 15 µm, 20 µm, 25 µm, 30 µm, 40 µm, 50 µm, 75 µm, 100 µm, 125 µm, 150 µm or 200 µm, or any range of values therebetween. In some embodiments, the hydroxyapatite has a mean particle size of, or of about, 10 nm, 20 nm, 30 nm, 40 nm, 50 nm, 60 nm, 70 nm, 80 nm, 90 nm, 0.1 µm, 0.15 µm, 0.2 µm, 0.3 µm, 0.4 µm, 0.5 µm, 0.8 µm, 1 µm, 2 µm, 5 µm, 8 µm, 10 µm, 15 µm, 20 µm, 25 µm, 30 µm, 40 µm, 50 µm, 75 µm, 100 µm, 125 µm, 150 µm or 200 µm, or any range of values therebetween. In some embodiments, the hydroxyapatite particles are spherical-shaped, near spherical-shaped, acircular shaped, short bar-shaped, rod-shaped and/or needle-shaped.

Fluoride may be utilized to prevent tooth decay, strengthen enamel, and increase the rate of remineralization. In some embodiments, the composition comprises fluoride of, of about, of at least, or at least about, 0.01 wt. %, 0.011 wt. %, 0.012 wt. %, 0.013 wt. %, 0.014 wt. %, 0.015 wt. %, 0.016 wt. %, 0.017 wt. %, 0.018 wt. %, 0.019 wt. %, 0.02 wt. %, 0.021 wt. %, 0.022 wt. %, 0.023 wt. %, 0.024 wt. %, 0.025 wt. %, 0.026 wt. %, 0.027 wt. %, 0.028 wt. %, 0.029 wt. %, 0.03 wt. %, 0.04 wt. %, 0.05 wt. %, 0.06 wt. %, 0.07 wt. %, 0.08 wt. %, 0.09 wt. %, 0.1 wt. %, 0.11 wt. %, 0.12 wt. %, 0.13 wt. %, 0.14 wt. %, 0.15 wt. %, 0.16 wt. %, 0.17 wt. %, 0.18 wt. %, 0.19 wt. %, 0.2 wt. %, 0.21 wt. %, 0.22 wt. %, 0.23 wt. %, 0.24 wt. %, 0.25 wt. %, 0.26 wt. %, 0.27 wt. %, 0.28 wt. %, 0.29 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, 3 wt. %, 3.1 wt. %, 3.2 wt. %, 3.3 wt. %, 3.4 wt. %, 3.5 wt. %, 3.6 wt. %, 3.7 wt. %, 3.8 wt. %, 3.9 wt. %, 4 wt. %, 4.1 wt. %, 4.2 wt. %, 4.3 wt. %, 4.4 wt. %, 4.5 wt. %, 4.6 wt. %, 4.7 wt. %, 4.8 wt. %, 4.9 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, or 20 wt. %, or any range of values therebetween. For example, in some embodiments, the amount of fluoride in the composition is or is about in any one of the following ranges: 0.01-0.03 wt. %, 0.019-0.021 wt. %, 0.2-0.3 wt. %, 0.22-0.26 wt. %, 0.01-1 wt. %, 0.1-1 wt. %, or 1-5 wt. % (based on total weight of the composition). In some embodiments, the combination of fluoride and hydroxyapatite in a composition synergistically and advantageously increases cavity protection and improves remineralization. In some embodiments, the composition is free or substantially free of fluoride.

Calcium carbonate and/or dicalcium phosphate may be utilized to assist in tooth remineralization. In some embodiments, the composition comprises calcium carbonate of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, 3 wt. %, 3.1 wt. %, 3.2 wt. %, 3.3 wt. %, 3.4 wt. %, 3.5 wt. %, 3.6 wt. %, 3.7 wt. %, 3.8 wt. %, 3.9 wt. % or 4 wt. %, or any range of values therebetween. In some embodiments, the composition comprises dicalcium phosphate of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, 3 wt. %, 3.1 wt. %, 3.2 wt. %, 3.3 wt. %, 3.4 wt. %, 3.5 wt. %, 3.6 wt. %, 3.7 wt. %, 3.8 wt. %, 3.9 wt. % or 4 wt. %, or any range of values therebetween. In some embodiments, the composition is free or substantially free of calcium carbonate and/or dicalcium phosphate.

Vitamin D (e.g., vitamin D3) may be utilized to assist bone and tooth mineralization, for example such as the minerals and compounds of hydroxyapatite. In some embodiments, the composition comprises vitamin D (e.g., vitamin D3) in, in about, in at least, or in at least about, 0.00001 wt. %, 0.00002 wt. %, 0.000025 wt. %, 0.00003 wt. %, 0.00004 wt. %, 0.00005 wt. %, 0.00006 wt. %, 0.00007 wt. %, 0.00008 wt. %, 0.00009 wt. %, 0.0001 wt. %, 0.0002 wt. %, 0.0003 wt. %, 0.0004 wt. %, 0.0005 wt. %, 0.0006 wt. %, 0.0007 wt. %, 0.0008 wt. %, 0.0009 wt. %, 0.001 wt. %, 0.0011 wt. %, 0.0012 wt. %, 0.0013 wt. %, 0.0014 wt. %, 0.0015 wt. %, 0.0016 wt. %, 0.0017 wt. %, 0.0018 wt. %, 0.0019 wt. %, 0.002 wt. %, 0.0025 wt. %, 0.003 wt. %, 0.0035 wt. %, 0.004 wt. %, 0.0045 wt. %, 0.005 wt. %, 0.0055 wt. %, 0.006 wt. %, 0.0065 wt. %, 0.007 wt. %, 0.0075 wt. %, 0.008 wt. %, 0.0085 wt. %, 0.009 wt. %, 0.0095 wt. % or 0.01 wt. %, or any range of values therebetween. For example, in some embodiments, the amount of vitamin D3 in the mixture is in any one of the following ranges: 0.0001-0.001 wt. %, 0.001-0.002 wt. %, 0.0010-0.0020 wt. %, 0.0011-0.0019 wt. %, 0.0012-0.0018 wt. %, 0.0013-0.0017 wt. %, 0.0014-0.0016 wt. %, 0.002-0.003 wt. %, 0.003-0.004 wt. %, 0.004-0.005 wt. %, 0.005-0.006 wt. %, 0.006-0.007 wt. %, 0.007-0.008 wt. %, 0.008-0.009 wt. % or 0.009-0.01 wt. % (based on total weight of the composition). In some embodiments, the amount of vitamin D3 in the mixture is within the daily dosage allowance of vitamin D3.

Vitamin K (e.g., vitamin K2) may assist in reducing calculus and promote proper bone growth, reducing conditions of septum deviation. Furthermore, Vitamin K may be utilized in the composition in conjunction with hydroxyapatite and/or vitamin D (e.g. vitamin D3) to promote bone and tooth mineralization. In some embodiments, the composition comprises vitamin K (e.g., vitamin K2) in, in about, in at least, or in at least about, 0.00001 wt. %, 0.00002 wt. %, 0.00003 wt. %, 0.00004 wt. %, 0.00005 wt. %, 0.00006 wt. %, 0.00007 wt. %, 0.00008 wt. %, 0.00009 wt. %, 0.0001 wt. %, 0.0002 wt. %, 0.0003 wt. %, 0.0004 wt. %, 0.0005 wt. %, 0.0006 wt. %, 0.0007 wt. %, 0.0008 wt. %, 0.0009 wt. %, 0.001 wt. %, 0.0011 wt. %, 0.0012 wt. %, 0.0013 wt. %, 0.0014 wt. %, 0.0015 wt. %, 0.0016 wt. %, 0.0017 wt. %, 0.0018 wt. %, 0.0019 wt. %, 0.002 wt. %, 0.0021 wt. %, 0.0022 wt. %, 0.0023 wt. %, 0.0024 wt. %, 0.0025 wt. %, 0.0026 wt. %, 0.0027 wt. %, 0.0028 wt. %, 0.0029 wt. %, 0.003 wt. %, 0.004 wt. %, 0.005 wt. %, 0.006 wt. %, 0.007 wt. %, 0.008 wt. %, 0.009 wt. %, 0.01 wt. %, 0.011 wt. %, 0.012 wt. %, 0.013 wt. %, 0.014 wt. %, 0.015 wt. %, 0.016 wt. %, 0.017 wt. %, 0.018 wt. %, 0.019 wt. %, 0.02 wt. %, 0.021 wt. %, 0.022 wt. %, 0.023 wt. %, 0.024 wt. %, 0.025 wt. %, 0.026 wt. %, 0.027 wt. %, 0.028 wt. %, 0.029 wt. %, 0.03 wt. %, %, 0.031 wt. %, 0.032 wt. %, 0.033 wt. %, 0.034 wt. %, 0.035 wt. %, 0.036 wt. %, 0.037 wt. %, 0.038 wt. %, 0.039 wt. %, 0.04 wt. %, %, 0.041 wt. %, 0.042 wt. %, 0.043 wt. %, 0.044 wt. %, 0.045 wt. %, 0.046 wt. %, 0.047 wt. %, 0.048 wt. %, 0.049 wt. % or 0.05 wt. %, or any range of values therebetween. For example, in some embodiments, the amount of vitamin K2 in the composition is in any one of the following ranges: 0.0001-0.001 wt. %, 0.001-0.002 wt. %, 0.002-0.003 wt. %, 0.003-0.012 wt. %, 0.004-0.011 wt. %, 0.005-0.01 wt. %, 0.006-0.009 wt. %, 0.007-0.008 wt. %, 0.01-0.02 wt. %, 0.02-0.03 wt. %, 0.03-0.04 wt. % or 0.04-0.05 wt. % (based on total weight of composition). In some embodiments, the amount of vitamin K2 in the mixture is within the daily dosage allowance of vitamin K2.

In some embodiments, the molar ratio of hydroxyapatite:vitamin D (e.g., hydroxyapatite:vitamin D3) is, is about, is greater than, or is greater than about, 7,000:1, 7,100:1, 7,200:1, 7,300:1, 7,400:1, 7,500:1, 7,600:1, 7,650:1, 7,656:1, 7,700:1, 7,800:1, 7,900:1 or 8,000:1, or any range of values therebetween. For example, in some embodiments the molar ratio of hydroxyapatite:vitamin D3 is about 7,600:1 to about 7,700:1, is about 7,650:1, or is 7,656:1. In some embodiments, the molar ratio of hydroxyapatite:vitamin K (e.g., hydroxyapatite:vitamin K2) is, is about, is greater than, or is greater than about, 1,500:1, 1,600:1, 1,700:1, 1,800:1, 1,900:1, 2,000:1, 2,100:1, 2,200:1, 2,210:1, 2,212:1, 2,250:1, 2,300:1, 2,400:1, 2,500:1, 2,600:1, 2,700:1, 2,800:1, 2,900:1 or 3,000:1, or any range of values therebetween. For example, in some embodiments the molar ratio of hydroxyapatite:vitamin K2 is about 2,100:1 to about 2,200:1, is about 2,210:1, or is 2,212:1. In some embodiments, the molar ratio of vitamin D:vitamin K (e.g., vitamin D3:vitamin K2) is, is about, is greater than, or is greater than about, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14 or 1:15, or any range of values therebetween. For example, in some embodiments the molar ratio of vitamin D3:vitamin K2 is about 1:1 to about 1:15, is about 1:5, or is 1:10. In some embodiments, recommended daily allowance of vitamin D3 and vitamin K2 are used to determine the molar ratio and/or amounts of vitamin D3 and vitamin K2.

Vitamin A may be utilized to promote gum health and as a nutrient for tooth enamel. Vitamin A may also be utilized in conjunction with hydroxyapatite, Vitamin D (e.g., vitamin D3), and Vitamin K (e.g., vitamin K2) to assist bone and tooth mineralization. In some embodiments, the composition comprises vitamin A in, in about, in at least, or in at least about, 0.00001 wt. %, 0.00002 wt. %, 0.00003 wt. %, 0.00004 wt. %, 0.00005 wt. %, 0.00006 wt. %, 0.00007 wt. %, 0.00008 wt. %, 0.00009 wt. %, 0.0001 wt. %, 0.0002 wt. %, 0.0003 wt. %, 0.0004 wt. %, 0.0005 wt. %, 0.0006 wt. %, 0.0007 wt. %, 0.0008 wt. %, 0.0009 wt. %, 0.001 wt. %, 0.0011 wt. %, 0.0012 wt. %, 0.0013 wt. %, 0.0014 wt. %, 0.0015 wt. %, 0.0016 wt. %, 0.0017 wt. %, 0.0018 wt. %, 0.0019 wt. %, 0.002 wt. %, 0.0021 wt. %, 0.0022 wt. %, 0.0023 wt. %, 0.0024 wt. %, 0.0025 wt. %, 0.0026 wt. %, 0.0027 wt. %, 0.0028 wt. %, 0.0029 wt. %, 0.003 wt. %, 0.004 wt. %, 0.005 wt. %, 0.006 wt. %, 0.007 wt. %, 0.008 wt. %, 0.009 wt. %, 0.01 wt. %, 0.011 wt. %, 0.012 wt. %, 0.013 wt. %, 0.014 wt. %, 0.015 wt. %, 0.016 wt. %, 0.017 wt. %, 0.018 wt. %, 0.019 wt. %, 0.02 wt. %, %, 0.021 wt. %, 0.022 wt. %, 0.023 wt. %, 0.024 wt. %, 0.025 wt. %, 0.026 wt. %, 0.027 wt. %, 0.028 wt. %, 0.029 wt. %, 0.03 wt. %, %, 0.031 wt. %, 0.032 wt. %, 0.033 wt. %, 0.034 wt. %, %, 0.035 wt. %, 0.036 wt. %, 0.037 wt. %, 0.038 wt. %, 0.039 wt. %, 0.04 wt. %, %, 0.041 wt. %, 0.042 wt. %, 0.043 wt. %, 0.044 wt. %, 0.045 wt. %, 0.046 wt. %, 0.047 wt. %, 0.048 wt. %, 0.049 wt. % or 0.05 wt. %, or any range of values therebetween. For example, in some embodiments, the amount of vitamin A in the mixture is in any one of the following ranges: 0.0001-0.001 wt. %, 0.001-0.002 wt. %, 0.0010-0.0020 wt. %, 0.0011-0.0019 wt. %, 0.0012-0.0018 wt. %, 0.0013-0.0017 wt. %, 0.0014-0.0016 wt. %, 0.002-0.003 wt. %, 0.003-0.004 wt. %, 0.004-0.005 wt. %, 0.005-0.006 wt. %, 0.006-0.007 wt. %, 0.007-0.008 wt. %, 0.008-0.009 wt. % or 0.009-0.01 wt. % (based on total weight of the composition). In some embodiments, the amount of vitamin A in the mixture is within the daily dosage allowance of vitamin A.

Anti-inflammatory agents are generally used to reduce gingival inflammation, reduce periodontal pain, and promote overall gingiva health. In some embodiments, the anti-inflammatory agents may be selected from methylsulfonylmethane, vitamin C, cranberry seed oil, sodium gluconate, or a mixture thereof. In some embodiments, the anti-inflammatory agents may comprise methylsulfonylmethane, vitamin C and cranberry seed oil. In some embodiments, the anti-inflammatory agents may comprise methylsulfonylmethane and vitamin C. In some embodiments, the anti-inflammatory agents may comprise methylsulfonylmethane and cranberry seed oil. In some embodiments, the anti-inflammatory agents may comprise vitamin C and cranberry seed oil.

Methylsulfonylmethane may be utilized to assist in reducing inflammation, promote the immune system, and/or combat microbial infections. In some embodiments, the composition comprises methylsulfonylmethane of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, 3 wt. %, 3.1 wt. %, 3.2 wt. %, 3.3 wt. %, 3.4 wt. %, 3.5 wt. %, 3.6 wt. %, 3.7 wt. %, 3.8 wt. %, 3.9 wt. %, 4 wt. %, 4.1 wt. %, 4.2 wt. %, 4.3 wt. %, 4.4 wt. %, 4.5 wt. %, 4.6 wt. %, 4.7 wt. %, 4.8 wt. %, 4.9 wt. % or 5 wt. %, or any range of values therebetween. For example, in some embodiments, the amount of methylsulfonylmethane in the composition is or is about in any one of the following ranges: 0.01-0.1 wt. %, 0.1-0.5 wt. %, 0.5-1 wt. %, 0.1-1 wt. %, 0.1-1.5 wt. % or 1-5 wt. % (based on total weight of the composition).

Vitamin C may be utilized to assist in reducing inflammation, strengthen gums and soft tissues and prevent gum disease. In some embodiments, the composition comprises vitamin C of, of about, of at least, or at least about, 0.001 wt. %, 0.002 wt. %, 0.003 wt. %, 0.004 wt. %, 0.005 wt. %, 0.006 wt. %, 0.007 wt. %, 0.008 wt. %, 0.009 wt. %, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.11 wt. %, 0.12 wt. %, 0.13 wt. %, 0.14 wt. %, 0.15 wt. %, 0.16 wt. %, 0.17 wt. %, 0.18 wt. %, 0.19 wt. %, 0.2 wt. %, 0.21 wt. %, 0.22 wt. %, 0.23 wt. %, 0.24 wt. %, 0.25 wt. %, 0.26 wt. %, 0.27 wt. %, 0.28 wt. %, 0.29 wt. %, 0.3 wt. %, 0.31 wt. %, 0.32 wt. %, 0.33 wt. %, 0.34 wt. %, 0.35 wt. %, 0.36 wt. %, 0.37 wt. %, 0.38 wt. %, 0.39 wt. %, 0.4 wt. %, 0.41 wt. %, 0.42 wt. %, 0.43 wt. %, 0.44 wt. %, 0.45 wt. %, 0.46 wt. %, 0.47 wt. %, 0.48 wt. %, 0.49 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. % or 2 wt. %, or any range of values therebetween. For example, in some embodiments, the amount of vitamin C in the composition is or is about in any one of the following ranges: 0.01-0.1 wt. %, 0.1-0.5 wt. %, 0.5-1 wt. %, 0.01-1 wt. %, 0.1-1 wt. % or 1-5 wt. % (based on total weight of the composition).

Cranberry seed oil may be utilized to assist in reducing inflammation and/or as a prebiotic. In some embodiments, the composition comprises cranberry seed oil of, of about, of at least, or at least about, 0.001 wt. %, 0.002 wt. %, 0.003 wt. %, 0.004 wt. %, 0.005 wt. %, 0.006 wt. %, 0.007 wt. %, 0.008 wt. %, 0.009 wt. %, 0.01 wt. %, 0.02 wt. %, 0.03 wt. %, 0.031 wt. %, 0.032 wt. %, 0.033 wt. %, 0.034 wt. %, 0.035 wt. %, 0.036 wt. %, 0.037 wt. %, 0.038 wt. %, 0.039 wt. %, 0.04 wt. %, 0.041 wt. %, 0.042 wt. %, 0.043 wt. %, 0.044 wt. %, 0.045 wt. %, 0.046 wt. %, 0.047 wt. %, 0.048 wt. %, 0.049 wt. %, 0.05 wt. %, 0.051 wt. %, 0.052 wt. %, 0.053 wt. %, 0.054 wt. %, 0.055 wt. %, 0.056 wt. %, 0.057 wt. %, 0.058 wt. %, 0.059 wt. %, 0.06 wt. %, 0.061 wt. %, 0.062 wt. %, 0.063 wt. %, 0.064 wt. %, 0.065 wt. %, 0.066 wt. %, 0.067 wt. %, 0.068 wt. %, 0.069 wt. %, 0.07 wt. %, 0.08 wt. %, 0.09 wt. %, 0.1 wt. %, 0.11 wt. %, 0.12 wt. %, 0.13 wt. %, 0.14 wt. %, 0.15 wt. %, 0.16 wt. %, 0.17 wt. %, 0.18 wt. %, 0.19 wt. %, 0.2 wt. %, 0.21 wt. %, 0.22 wt. %, 0.23 wt. %, 0.24 wt. %, 0.25 wt. %, 0.26 wt. %, 0.27 wt. %, 0.28 wt. %, 0.29 wt. %, 0.3 wt. %, 0.31 wt. %, 0.32 wt. %, 0.33 wt. %, 0.34 wt. %, 0.35 wt. %, 0.36 wt. %, 0.37 wt. %, 0.38 wt. %, 0.39 wt. %, 0.4 wt. %, 0.41 wt. %, 0.42 wt. %, 0.43 wt. %, 0.44 wt. %, 0.45 wt. %, 0.46 wt. %, 0.47 wt. %, 0.48 wt. %, 0.49 wt. %, 0.5 wt. %, 0.6 wt. %, 0.7 wt. %, 0.8 wt. %, 0.9 wt. %, 1 wt. %, 2 wt. %, 3 wt. %, 4 wt. % or 5 wt. %, or any range of values therebetween. For example, in some embodiments, the amount of cranberry seed oil in the composition is or is about in any one of the following ranges: 0.001-0.01 wt. %, 0.01-0.1 wt. %, 0.1-1 wt. %, 0.01-1 wt. %, 0.001-0.1 wt. % or 1-5 wt. % (based on total weight of the composition).

In some embodiments, the molar ratio of methylsulfonylmethane:vitamin C is, is about, is greater than, or is greater than about, 20:1, 19:1, 18.7:1, 18:1, 17:1, 16:1, 15:1, 14:1, 13:1, 12:1, 11:1, 10:1, 9.3:1, 9:1, 8:1, 7:1, 6:1, 5:1, 4:1, 3:1, 2:1 or 1:1, or any range of values therebetween. For example, in some embodiments the molar ratio of methylsulfonylmethane:vitamin C is about 20:1 to about 16:1, is about 11:1 to about 9:1, is about 6:1 to about 4:1, is about 18:1, is about 10:1, is about 5:1, is 18.7:1 or is 9.3:1. In some embodiments, recommended daily allowance of vitamin C is used to determine the molar ratio and/or amounts of vitamin C and methylsulfonylmethane.

A gluconate salt (e.g., sodium gluconate) may be utilized to prevent tooth decay and the growth of microbes. In some embodiments, the composition comprises a gluconate salt of, of about, of at least, or at least about, 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, 3 wt. %, 4 wt. %, 5 wt. %, 6 wt. %, 7 wt. %, 8 wt. %, 9 wt. % or 10 wt. %, or any range of values therebetween. For example, in some embodiments, the amount of a gluconate salt (e.g., sodium gluconate) in the composition is or is about in any one of the following ranges: 1-2 wt. %, 2-5 wt. %, 1.5-2.5 wt. % or 1-5 wt. % (based on total weight of the composition).

Prebiotic agents are generally used to promote beneficial oral bacteria, promote the long-term health of teeth and gums, and reduce bad breath. In some embodiments, the prebiotic agents may be selected from inulin, xylitol, erythritol, cranberry seed oil, xanthan gum, *stevia* leaf extract, or a mixture thereof. In some embodiments, the prebiotic agents may comprise xylitol, erythritol, *stevia* leaf extract, or a mixture thereof. In some embodiments, the prebiotic agents may comprise inulin, xylitol, erythritol, and cranberry seed oil. In some embodiments, the prebiotic agents may comprise xylitol, erythritol, and *stevia* leaf extract. In some embodiments, the prebiotic agents may comprise inulin, xylitol, and erythritol. In some embodiments, the prebiotic agents may comprise inulin and xylitol. In some embodiments, the prebiotic agents may comprise inulin and erythritol. In some embodiments, the prebiotic agents may comprise inulin and cranberry seed oil. In some embodiments, the prebiotic agents may comprise xylitol, erythritol, and cranberry seed oil. In some embodiments, the prebiotic agents may comprise xylitol and erythritol. In some embodiments, the prebiotic agents may comprise xylitol and cranberry seed oil. In some embodiments, the prebiotic agents may comprise erythritol and cranberry seed oil. In some embodiments, the prebiotic agents may comprise xylitol and *stevia* leaf extract. In some embodiments, the prebiotic agents may comprise erythritol and *stevia* leaf extract.

Inulin may be utilized as a prebiotic and/or to reduce halitosis. In some embodiments, the composition comprises inulin of, of about, of at least, or at least about, 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, 3 wt. %, 3.1 wt. %, 3.2 wt. %, 3.3 wt. %, 3.4 wt. %, 3.5 wt. %, 3.6 wt. %, 3.7 wt. %, 3.8 wt. %, 3.9 wt. %, 4 wt. %, 4.1 wt. %, 4.2 wt. %, 4.3 wt. %, 4.4 wt. %, 4.5 wt. %, 4.6 wt. %, 4.7 wt. %, 4.8 wt. %, 4.9 wt. %, 5 wt. %, 5.1 wt. %, 5.2 wt. %, 5.3 wt. %, 5.4 wt. %, 5.5 wt. %, 5.6 wt. %, 5.7 wt. %, 5.8 wt. %, 5.9 wt. %, 6 wt. %, 6.1 wt. %, 6.2 wt. %, 6.3 wt. %, 6.4 wt. %, 6.5 wt. %, 6.6 wt. %, 6.7 wt. %, 6.8 wt. %, 6.9 wt. %, 7 wt. %, 7.1 wt. %, 7.2 wt. %, 7.3 wt. %, 7.4 wt. %, 7.5 wt. %, 7.6 wt. %, 7.7 wt. %, 7.8 wt. %, 7.9 wt. %, 8 wt. %, 8.1 wt. %, 8.2 wt. %, 8.3 wt. %, 8.4 wt. %, 8.5 wt. %, 8.6 wt. %, 8.7 wt. %, 8.8 wt. %, 8.9 wt. %, 9 wt. %, 9.1 wt. %, 9.2 wt. %, 9.3 wt. %, 9.4 wt. %, 9.5 wt. %, 9.6 wt. %, 9.7 wt. %, 9.8 wt. %, 9.9 wt. %, 10 wt. %, 11 wt. %, 12 wt. %, 13 wt. %, 14 wt. %, 15 wt. %, 16 wt. %, 17 wt. %, 18 wt. %, 19 wt. % or 20 wt. %, or any range of values therebetween. For example, in some embodiments, the amount of inulin in the composition is or is about in any one of the following ranges: 0.1-1 wt. %, 1-5 wt. %, 5-10 wt. %, 1-10 wt. %, 10-20 wt. %, 2-8 wt. %, 3-7 wt. % or 4-6 wt. % (based on total weight of the composition).

Xylitol may be utilized as a prebiotic, flavoring agent, alkalizing agent, buffering agent, and/or to reduce cavities. In some embodiments, the composition comprises xylitol of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, 3 wt. %, 3.1 wt. %, 3.2 wt. %, 3.3 wt. %, 3.4 wt. %, 3.5 wt. %, 3.6 wt. %, 3.7 wt. %, 3.8 wt. %, 3.9 wt. %, 4 wt. %, 4.1 wt. %, 4.2 wt. %, 4.3 wt. %, 4.4 wt. %, 4.5 wt. %, 4.6 wt. %, 4.7 wt. %, 4.8 wt. %, 4.9 wt. %, 5 wt. %, 5.1 wt. %, 5.2 wt. %, 5.3 wt. %, 5.4 wt. %, 5.5 wt. %, 5.6 wt. %, 5.7 wt. %, 5.8 wt. %, 5.9 wt. %, 6 wt. %, 6.1 wt. %, 6.2 wt. %, 6.3 wt. %, 6.4 wt. %, 6.5 wt. %, 6.6 wt. %, 6.7 wt. %, 6.8 wt. %, 6.9 wt. %, 7 wt. %, 7.1 wt. %, 7.2 wt. %, 7.3 wt. %, 7.4 wt. %, 7.5 wt. %, 7.6 wt. %, 7.7 wt. %, 7.8 wt. %, 7.9 wt. %, 8 wt. %, 8.1 wt. %, 8.2 wt. %, 8.3 wt. %, 8.4 wt. %, 8.5 wt. %, 8.6 wt. %, 8.7 wt. %, 8.8 wt. %, 8.9 wt. %, 9 wt. %, 9.1 wt. %, 9.2 wt. %, 9.3 wt. %, 9.4 wt. %, 9.5 wt. %, 9.6 wt. %, 9.7 wt. %, 9.8 wt. %, 9.9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. % or 25 wt. %, or any range of values therebetween. For example, in some embodiments, the amount of xylitol in the composition is or is about in any one of the following ranges: 0.1-1 wt. %, 0.1-5 wt. %, 1-3 wt. %, 1-5 wt. %, 5-10 wt. %, 1-15 wt. %, 15-20 wt. %, 20-25 wt. %, 5-20 wt. %, 10-15 wt. %, 9-11 wt. % or 14-16 wt. % (based on total weight of the composition).

Erythritol may be utilized as a prebiotic, flavoring agent, alkalizing agent, buffering agent, for its cooling effect, and/or to reduce cavities. In some embodiments, the composition comprises erythritol of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, 3 wt. %, 3.1 wt. %, 3.2 wt. %, 3.3 wt. %, 3.4 wt. %, 3.5 wt. %, 3.6 wt. %, 3.7 wt. %, 3.8 wt. %, 3.9 wt. %, 4 wt. %, 4.1 wt. %, 4.2 wt. %, 4.3 wt. %, 4.4 wt. %, 4.5 wt. %, 4.6 wt. %, 4.7 wt. %, 4.8 wt. %, 4.9 wt. %, 5 wt. %, 5.1 wt. %, 5.2 wt. %, 5.3 wt. %, 5.4 wt. %, 5.5 wt. %, 5.6 wt. %, 5.7 wt. %, 5.8 wt. %, 5.9 wt. %, 6 wt. %, 6.1 wt. %, 6.2 wt. %, 6.3 wt. %, 6.4 wt. %, 6.5 wt. %, 6.6 wt. %, 6.7 wt. %, 6.8 wt. %, 6.9 wt. %, 7 wt. %, 7.1 wt. %, 7.2 wt. %, 7.3 wt. %, 7.4 wt. %, 7.5 wt. %, 7.6 wt. %, 7.7 wt. %, 7.8 wt. %, 7.9 wt. %, 8 wt. %, 8.1 wt. %, 8.2 wt. %, 8.3 wt. %, 8.4 wt. %, 8.5 wt. %, 8.6 wt. %, 8.7 wt. %, 8.8 wt. %, 8.9 wt. %, 9 wt. %, 9.1 wt. %, 9.2 wt. %, 9.3 wt. %, 9.4 wt. %, 9.5 wt. %, 9.6 wt. %, 9.7 wt. %, 9.8 wt. %, 9.9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. % or 25 wt. %, or any range of values therebetween. For example, in some embodiments, the amount of erythritol in the composition is or is about in any one of the following ranges: 0.01-1 wt. %, 0.1-1 wt. %, 0.1-5 wt. %, 0.5-2.5 wt. %, 0.1-3 wt. %, 0.01-3 wt. %, 1-5 wt. %, 5-10 wt. %, 10-15 wt. %, 15-20 wt. %, 20-25 wt. %, 5-20 wt. %, 1-15 wt. %, 9-11 wt. % or 14-16 wt. % (based on total weight of the composition).

Cranberry seed oil may also be utilized as a prebiotic. In some embodiments, the composition comprises cranberry seed oil of, of about, of at least, or at least about, 0.001 wt. %, 0.002 wt. %, 0.003 wt. %, 0.004 wt. %, 0.005 wt. %, 0.006 wt. %, 0.007 wt. %, 0.008 wt. %, 0.009 wt. %, 0.01 wt. %, 0.02 wt. %, 0.03 wt. %, 0.031 wt. %, 0.032 wt. %, 0.033 wt. %, 0.034 wt. %, 0.035 wt. %, 0.036 wt. %, 0.037 wt. %, 0.038 wt. %, 0.039 wt. %, 0.04 wt. %, 0.041 wt. %, 0.042 wt. %, 0.043 wt. %, 0.044 wt. %, 0.045 wt. %, 0.046 wt. %, 0.047 wt. %, 0.048 wt. %, 0.049 wt. %, 0.05 wt. %, 0.051 wt. %, 0.052 wt. %, 0.053 wt. %, 0.054 wt. %, 0.055 wt. %, 0.056 wt. %, 0.057 wt. %, 0.058 wt. %, 0.059 wt. %, 0.06 wt. %, 0.061 wt. %, 0.062 wt. %, 0.063 wt. %, 0.064 wt. %, 0.065 wt. %, 0.066 wt. %, 0.067 wt. %, 0.068 wt. %, 0.069 wt. %, 0.07 wt. %, 0.08 wt. %, 0.09 wt. %, 0.1 wt. %, 0.11 wt. %, 0.12 wt. %, 0.13 wt. %, 0.14 wt. %, 0.15 wt. %, 0.16 wt. %, 0.17 wt. %, 0.18 wt. %, 0.19 wt. %, 0.2 wt. %, 0.21 wt. %, 0.22 wt. %, 0.23 wt. %, 0.24 wt. %, 0.25 wt. %, 0.26 wt. %, 0.27 wt. %, 0.28 wt. %, 0.29 wt. %, 0.3 wt. %, 0.31 wt. %, 0.32 wt. %, 0.33 wt. %, 0.34 wt. %, 0.35 wt. %, 0.36 wt. %, 0.37 wt. %, 0.38 wt. %, 0.39 wt. %, 0.4 wt. %, 0.41 wt. %, 0.42 wt. %, 0.43 wt. %, 0.44 wt. %, 0.45 wt. %, 0.46 wt. %, 0.47 wt. %, 0.48 wt. %, 0.49 wt. %, 0.5 wt. %, 0.6 wt. %, 0.7 wt. %, 0.8 wt. %, 0.9 wt. %, 1 wt. %, 2 wt. %, 3 wt. %, 4 wt. % or 5 wt. %, or any range of values therebetween. For example, in some embodiments, the amount of cranberry seed oil in the composition is or is about in any one of the following ranges: 0.001-0.01 wt. %, 0.01-0.1 wt. %, 0.1-1 wt. %, 0.01-1 wt. %, 0.001-0.1 wt. % or 1-5 wt. % (based on total weight of the composition).

*Stevia* leaf extract may also be utilized as a prebiotic and/or may be utilized as a source of vitamins and minerals. In some embodiments, the prebiotic agent comprises *stevia* leaf extract of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. %, 3 wt. %, 3.1 wt. %, 3.2 wt. %, 3.3 wt. %, 3.4 wt. %, 3.5 wt. %, 3.6 wt. %, 3.7 wt. %, 3.8 wt. %, 3.9 wt. %, 4 wt. %, 4.1 wt. %, 4.2 wt. %, 4.3 wt. %, 4.4 wt. %, 4.5 wt. %, 4.6 wt. %, 4.7 wt. %, 4.8 wt. %, 4.9 wt. %, 5 wt. %, 5.1 wt. %, 5.2 wt. %, 5.3 wt. %, 5.4 wt. %, 5.5 wt. %, 5.6 wt. %, 5.7 wt. %, 5.8 wt. %, 5.9 wt. %, 6 wt. %, 6.1 wt. %, 6.2 wt. %, 6.3 wt. %, 6.4 wt. %, 6.5 wt. %, 6.6 wt. %, 6.7 wt. %, 6.8 wt. %, 6.9 wt. %, 7 wt. %, 7.1 wt. %, 7.2 wt. %, 7.3 wt. %, 7.4 wt. %, 7.5 wt. %, 7.6 wt. %, 7.7 wt. %, 7.8 wt. %, 7.9 wt. %, 8 wt. %, 8.1 wt. %, 8.2 wt. %, 8.3 wt. %, 8.4 wt. %, 8.5 wt. %, 8.6 wt. %, 8.7 wt. %, 8.8 wt. %, 8.9 wt. %, 9 wt. %, 9.1 wt. %, 9.2 wt. %, 9.3 wt. %, 9.4 wt. %, 9.5 wt. %, 9.6 wt. %, 9.7 wt. %, 9.8 wt. %, 9.9 wt. %, 10 wt. %, 11 wt. %, 12 wt. %, 13 wt. %, 14 wt. % or 15 wt. %, or any range of values therebetween. For example, in some embodiments, the amount of *stevia* leaf extract in the prebiotic agent is or is about in any one of the following ranges: 0.01-1 wt. %, 0.1-1 wt. %, 0.1-5 wt. %, 1-5 wt. %, 5-10 wt. %, 10-15 wt. %, 1-15 wt. %, 0.5-2.5 wt. %, 0.1-3 wt. % or 0.01-3 wt. % (based on total weight of the composition).

Alkalizing agents are generally used to raise the pH of a solution and/or balance and buffer the pH of a solution. In some embodiments, the alkalizing agents may be selected from sodium bicarbonate, xylitol, erythritol, or a mixture thereof. In some embodiments, the alkalizing agents may comprise sodium bicarbonate, xylitol, and erythritol. In some embodiments, the alkalizing agents may comprise sodium bicarbonate and xylitol. In some embodiments, the alkalizing agents may comprise sodium bicarbonate and erythritol. In some embodiments, the alkalizing agents may comprise xylitol and erythritol.

Sodium bicarbonate may be utilized as an alkalizing agent and/or a buffering agent. In some embodiments, the composition comprises sodium bicarbonate of, of about, of at least, or at least about, 0.01 wt. %, 0.05 wt. %, 0.1 wt. %, 0.15 wt. %, 0.2 wt. %, 0.25 wt. %, 0.3 wt. %, 0.35 wt. %, 0.4 wt. %, 0.45 wt. %, 0.5 wt. %, 0.55 wt. %, 0.6 wt. %, 0.65 wt. %, 0.7 wt. %, 0.75 wt. %, 0.8 wt. %, 0.85 wt. %, 0.9 wt. %, 0.95 wt. %, 1 wt. %, 1.05 wt. %, 1.1 wt. %, 1.15 wt. %, 1.2 wt. %, 1.25 wt. %, 1.3 wt. %, 1.35 wt. %, 1.4 wt. %, 1.45 wt. %, 1.5 wt. %, 1.55 wt. %, 1.6 wt. %, 1.65 wt. %, 1.7 wt. %, 1.75 wt. %, 1.8 wt. %, 1.85 wt. %, 1.9 wt. %, 1.95 wt. %, 2 wt. %, 2.05 wt. %, 2.1 wt. %, 2.15 wt. %, 2.2 wt. %, 2.25 wt. %, 2.3 wt. %, 2.35 wt. %, 2.4 wt. %, 2.45 wt. %, 2.5 wt. %, 2.55 wt. %, 2.6 wt. %, 2.65 wt. %, 2.7 wt. %, 2.75 wt. %, 2.8 wt. %, 2.85 wt. %, 2.9 wt. %, 2.95 wt. %, 3 wt. %, 3.05 wt. %, 3.1 wt. %, 3.15 wt. %, 3.2 wt. %, 3.25 wt. %, 3.3 wt. %, 3.35 wt. %, 3.4 wt. %, 3.45 wt. %, 3.5 wt. %, 3.55 wt. %, 3.6 wt. %, 3.65 wt. %, 3.7 wt. %, 3.75 wt. %, 3.8 wt. %, 3.85 wt. %, 3.9 wt. %, 3.95 wt. %, 4 wt. %, 4.05 wt. %, 4.1 wt. %, 4.15 wt. %, 4.2 wt. %, 4.25 wt. %, 4.3 wt. %, 4.35 wt. %, 4.4 wt. %, 4.45 wt. %, 4.5 wt. %, 4.55 wt.

%, 4.6 wt. %, 4.65 wt. %, 4.7 wt. %, 4.75 wt. %, 4.8 wt. %, 4.85 wt. %, 4.9 wt. %, 4.95 wt. %, 5 wt. %, 6 wt. %, 7 wt. %, 8 wt. %, 9 wt. % or 10 wt. %, or any range of values therebetween. For example, in some embodiments, the amount of sodium bicarbonate in the composition is or is about in any one of the following ranges: 0.01-0.1 wt. %, 0.1-1 wt. %, 1-2 wt. %, 0.5-1.5 wt. %, 1-5 wt. %, 0.1-2 wt. % or 0.1-5 wt. % (based on total weight of the composition).

Xylitol may also be utilized as an alkalizing agent and/or a buffering agent. In some embodiments, the composition comprises xylitol of, of about, of at least, or at least about, 1 wt. %, 2 wt. %, 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. % or 25 wt. %, or any range of values therebetween. For example, in some embodiments, the amount of xylitol in the composition is or is about in any one of the following ranges: 1-5 wt. %, 5-10 wt. %, 10-15 wt. %, 15-20 wt. %, 20-25 wt. %, 5-20 wt. %, 10-15 wt. %, 9-11 wt. % or 14-16 wt. % (based on total weight of the composition).

Erythritol may also be utilized as an alkalizing agent and/or a buffering agent. In some embodiments, the composition comprises erythritol of, of about, of at least, or at least about, 1 wt. %, 2 wt. %, 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. % or 25 wt. %, or any range of values therebetween. For example, in some embodiments, the amount of erythritol in the composition is or is about in any one of the following ranges: 1-5 wt. %, 5-10 wt. %, 10-15 wt. %, 15-20 wt. %, 20-25 wt. %, 5-20 wt. %, 10-15 wt. %, 9-11 wt. % or 14-16 wt. % (based on total weight of the composition).

In some embodiments, the oral hygiene composition further includes a solvent. In some embodiments, the solvent may be selected from water, glycerin, or a mixture thereof. In some embodiments, the solvent comprises water and glycerin. In some embodiments, the composition comprises water in, in about, in at least, or in least about, 1 wt. %, 5 wt. %, 10 wt. %, 15 wt. %, 20 wt. %, 25 wt. %, 30 wt. %, 35 wt. %, 40 wt. %, 45 wt. %, 50 wt. %, 55 wt. %, 60 wt. %, 65 wt. %, 70 wt. %, 75 wt. %, 80 wt. % or 85 wt. %, or any range of values therebetween. For example, in some embodiments, the amount of water in the composition is or is about in any one of the following ranges: 10-15 wt. %, 15-20 wt. %, 20-25 wt. %, 55-60 wt. %, 60-65 wt. %, 65-70 wt. % or 70-75 wt. % (based on total weight of the composition). In some embodiments, the composition comprises glycerin in, in about, in at least, or in at least about, 0.1 wt. %, 0.5 wt. %, 1 wt. %, 1.5 wt. %, 2 wt. %, 2.5 wt. %, 3 wt. %, 3.5 wt. %, 4 wt. %, 4.5 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 15.5 wt. %, 16 wt. %, 16.5 wt. %, 17 wt. %, 17.5 wt. %, 18 wt. %, 18.5 wt. %, 19 wt. %, 19.5 wt. %, 20 wt. %, 21 wt. %, 22 wt. %, 23 wt. %, 24 wt. % or 25 wt. %, or any range of values therebetween. For example, in some embodiments, the amount of glycerin in the composition is or is about in any one of the following ranges: 0.1-1 wt. %, 1-2 wt. %, 1-3 wt. %, 1-5 wt. %, 5-15 wt. %, 10-15 wt. %, 15-20 wt. %, 20-25 wt. %, 5-20 wt. %, 10-15 wt. % or 16-18 wt. % (based on total weight of the composition). In some embodiments, the solvent is recited to be the balance of the composition.

In some embodiments, the oral hygiene composition further includes a cleaning agent, which are generally used as microscopic, abrasive polishing agent. In some embodiments, the cleaning agent may be selected from hydrated silica, *Quillaja saponaria* extract, or a mixture thereof. In some embodiments, the cleaning agent comprises hydrated silica and *Quillaja saponaria* extract. Hydrated silica may be utilized as a thickening and/or cleaning agent. In some embodiments, the composition comprises hydrated silica of, of about, of at least, or at least about, 1 wt. %, 2 wt. %, 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. % or 25 wt. %, or any range of values therebetween. For example, in some embodiments, the amount of hydrated silica in the composition is or is about in any one of the following ranges: 1-5 wt. %, 5-10 wt. %, 10-15 wt. %, 15-20 wt. %, 20-25 wt. %, 10-20 wt. % or 14-16 wt. % (based on total weight of the composition).

*Quillaja saponaria* extract may be utilized as a foaming and/or cleaning agent. In some embodiments, the composition comprises *Quillaja saponaria* extract of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.11 wt. %, 0.12 wt. %, 0.13 wt. %, 0.14 wt. %, 0.15 wt. %, 0.16 wt. %, 0.17 wt. %, 0.18 wt. %, 0.19 wt. %, 0.2 wt. %, 0.21 wt. %, 0.22 wt. %, 0.23 wt. %, 0.24 wt. %, 0.25 wt. %, 0.26 wt. %, 0.27 wt. %, 0.28 wt. %, 0.29 wt. %, 0.3 wt. %, 0.31 wt. %, 0.32 wt. %, 0.33 wt. %, 0.34 wt. %, 0.35 wt. %, 0.36 wt. %, 0.37 wt. %, 0.38 wt. %, 0.39 wt. %, 0.4 wt. %, 0.41 wt. %, 0.42 wt. %, 0.43 wt. %, 0.44 wt. %, 0.45 wt. %, 0.46 wt. %, 0.47 wt. %, 0.48 wt. %, 0.49 wt. %, 0.5 wt. %, 0.51 wt. %, 0.52 wt. %, 0.53 wt. %, 0.54 wt. %, 0.55 wt. %, 0.56 wt. %, 0.57 wt. %, 0.58 wt. %, 0.59 wt. %, 0.6 wt. %, 0.61 wt. %, 0.62 wt. %, 0.63 wt. %, 0.64 wt. %, 0.65 wt. %, 0.66 wt. %, 0.67 wt. %, 0.68 wt. %, 0.69 wt. %, 0.7 wt. %, 0.71 wt. %, 0.72 wt. %, 0.73 wt. %, 0.74 wt. %, 0.75 wt. %, 0.76 wt. %, 0.77 wt. %, 0.78 wt. %, 0.79 wt. %, 0.8 wt. %, 0.81 wt. %, 0.82 wt. %, 0.83 wt. %, 0.84 wt. %, 0.85 wt. %, 0.86 wt. %, 0.87 wt. %, 0.88 wt. %, 0.89 wt. %, 0.9 wt. %, 0.91 wt. %, 0.92 wt. %, 0.93 wt. %, 0.94 wt. %, 0.95 wt. %, 0.96 wt. %, 0.97 wt. %, 0.98 wt. %, 0.99 wt. %, 1 wt. %, 2 wt. %, 3 wt. %, 4 wt. % or 5 wt. %, or any range of values therebetween. For example, in some embodiments, the amount of *Quillaja saponaria* extract in the composition is or is about in any one of the following ranges: 0.01-0.1 wt. %, 0.1-1 wt. %, 1-3 wt. %, 0.1-0.5 wt. %, 0.01-0.5 wt. %, 0.2-0.4 wt. % or 0.1-0.9 wt. % (based on total weight of the composition).

In some embodiments, the oral hygiene composition further includes a flavoring agent. Flavoring agents may be utilized to assist in providing a favorable taste and/or smell and/or as a taste masking agent. In some embodiments, the flavoring agent may be selected from xylitol, erythritol, *stevia*, peppermint flavor, spearmint flavor, strawberry flavor, vanilla flavor, chocolate flavor, cherry flavor, blueberry flavor, bubblegum flavor, grape flavor, apricot flavor, clove flavor, ginger flavor, wintergreen flavor, mango flavor, fennel flavor, orange flavor, black currant flavor, watermelon flavor, cinnamon flavor, or a mixture thereof. In some embodiments, the composition comprises a flavoring agent of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.11 wt. %, 0.12 wt. %, 0.13 wt. %, 0.14 wt. %, 0.15 wt. %, 0.16 wt. %, 0.17 wt. %, 0.18 wt. %, 0.19 wt. %, 0.2 wt. %, 0.21 wt. %, 0.22 wt. %, 0.23 wt. %, 0.24 wt. %, 0.25 wt. %, 0.26 wt. %, 0.27 wt. %, 0.28 wt. %, 0.29 wt. %, 0.3 wt. %, 0.31 wt. %, 0.32 wt. %, 0.33 wt. %, 0.34 wt. %, 0.35 wt. %, 0.36 wt. %, 0.37 wt. %, 0.38 wt. %, 0.39 wt. %, 0.4 wt. %, 0.41 wt. %, 0.42 wt. %, 0.43 wt. %, 0.44 wt. %, 0.45 wt. %, 0.46 wt. %, 0.47 wt. %, 0.48 wt. %, 0.49 wt. %, 0.5 wt. %, 0.51 wt. %, 0.52 wt. %, 0.53 wt. %, 0.54 wt. %, 0.55 wt. %, 0.56 wt. %, 0.57 wt. %, 0.58 wt. %, 0.59 wt. %, 0.6 wt. %, 0.61 wt. %, 0.62 wt. %, 0.63 wt. %, 0.64 wt. %, 0.65 wt. %, 0.66 wt. %, 0.67 wt. %, 0.68 wt. %, 0.69 wt. %, 0.7 wt. %, 0.71 wt. %, 0.72 wt. %, 0.73 wt. %, 0.74 wt. %, 0.75 wt. %, 0.76 wt. %, 0.77 wt. %, 0.78 wt. %, 0.79 wt. %, 0.8 wt. %, 0.81 wt. %, 0.82 wt. %, 0.83 wt. %, 0.84 wt. %, 0.85 wt. %, 0.86 wt. %, 0.87 wt. %, 0.88 wt. %, 0.89 wt. %, 0.9 wt. %, 0.91 wt. %, 0.92 wt. %, 0.93 wt. %, 0.94 wt. %, 0.95 wt. %, 0.96 wt. %, 0.97 wt. %, 0.98 wt. %, 0.99 wt. %, 1 wt. %, 2 wt. %, 3 wt. %, 4 wt. % or 5 wt. %, or any range of values therebetween. For example, in some embodiments, the amount of a flavoring agent in the composition is or is about in any one of the following ranges: 0.01-0.1 wt. %, 0.1-0.3 wt. %, 0.1-0.5 wt. %, 0.01-0.5 wt. %, 0.1-0.3 wt. % or 0.1-0.9 wt. % (based on total weight of the composition).

In some embodiments, the oral hygiene composition further includes a coloring agent. In some embodiments, the coloring agent is a food coloring agent. In some embodiments, the composition comprises a coloring agent of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.11 wt. %, 0.12 wt. %, 0.13 wt. %, 0.14 wt. %, 0.15 wt. %, 0.16 wt. %, 0.17 wt. %, 0.18 wt. %, 0.19 wt. %, 0.2 wt. %, 0.21 wt. %, 0.22 wt. %, 0.23 wt. %, 0.24 wt. %, 0.25 wt. %, 0.26 wt. %, 0.27 wt. %, 0.28 wt. %, 0.29 wt. %, 0.3 wt. %, 0.31 wt. %, 0.32 wt. %, 0.33 wt. %, 0.34 wt. %, 0.35 wt. %, 0.36 wt. %, 0.37 wt. %, 0.38 wt. %, 0.39 wt. %, 0.4 wt. %, 0.41 wt. %, 0.42 wt. %, 0.43 wt. %, 0.44 wt. %, 0.45 wt. %, 0.46 wt. %, 0.47 wt. %, 0.48 wt. %, 0.49 wt. %, 0.5 wt. %, 0.51 wt. %, 0.52 wt. %, 0.53 wt. %, 0.54 wt. %, 0.55 wt. %, 0.56 wt. %, 0.57 wt. %, 0.58 wt. %, 0.59 wt. %, 0.6 wt. %, 0.61 wt. %, 0.62 wt. %, 0.63 wt. %, 0.64 wt. %, 0.65 wt. %, 0.66 wt. %, 0.67 wt. %, 0.68 wt. %, 0.69 wt. %, 0.7 wt. %, 0.71 wt. %, 0.72 wt. %, 0.73 wt. %, 0.74 wt. %, 0.75 wt. %, 0.76 wt. %, 0.77 wt. %, 0.78 wt. %, 0.79 wt. %, 0.8 wt. %, 0.81 wt. %, 0.82 wt. %, 0.83 wt. %, 0.84 wt. %, 0.85 wt. %, 0.86 wt. %, 0.87 wt. %, 0.88 wt. %, 0.89 wt. %, 0.9 wt. %, 0.91 wt. %, 0.92 wt. %, 0.93 wt. %, 0.94 wt. %, 0.95 wt. %, 0.96 wt. %, 0.97 wt. %, 0.98 wt. %, 0.99 wt. %, 1 wt. %, 1.5 wt. %, 2 wt. %, 3 wt. %, 4 wt. % or 5 wt. %, or any range of values therebetween. For example, in some embodiments, the amount of a coloring agent in the composition is or is about in any one of the following ranges: 0.01-0.1 wt. %, 1-3 wt. %, 0.1-2 wt. %, 0.5-1.5 wt. %, 0.1-0.3 wt. % or 0.1-0.9 wt. % (based on total weight of the composition).

Compositional Forms

The oral hygiene composition may be in the form of a toothpaste, mouthwash, or mouth spray.

In some embodiments, the oral hygiene toothpaste composition may comprise water, hydrated silica, hydroxyapatite, glycerin, erythritol, xylitol, inulin, methylsulfonylmethane, calcium carbonate, *Quillaja saponaria* extract, *stevia* leaf extract, dicalcium phosphate, xanthan gum, vitamin C, sodium gluconate, cranberry seed oil, vitamin D3, vitamin K2, flavoring agent, or a mixture thereof. In some embodiments, the oral hygiene toothpaste composition may comprise water, hydrated silica, hydroxyapatite, glycerin, erythritol, xylitol, inulin, methylsulfonylmethane, calcium carbonate, *Quillaja saponaria* extract, *stevia* leaf extract, dicalcium phosphate, xanthan gum, vitamin C, sodium gluconate, cranberry seed oil, vitamin D3, vitamin K2, and a flavoring agent. In some embodiments, the oral hygiene toothpaste composition may comprise water, hydrated silica, hydroxyapatite, glycerin, erythritol, xylitol, inulin, methylsulfonylmethane, *Quillaja saponaria* extract, *stevia* leaf extract, xanthan gum, vitamin C, sodium gluconate, cranberry seed oil, vitamin D3, vitamin K2, sodium fluoride, flavoring agent, or a mixture thereof. In some embodiments, the oral hygiene toothpaste composition may comprise water, hydrated silica, hydroxyapatite, glycerin, erythritol, xylitol, inulin, methylsulfonylmethane, *Quillaja saponaria* extract, *stevia* leaf extract, xanthan gum, vitamin C, sodium gluconate, cranberry seed oil, vitamin D3, vitamin K2, sodium fluoride, and a flavoring agent.

In some embodiments, the oral hygiene mouthwash composition may comprise water, xylitol, erythritol, inulin, hydroxyapatite, glycerin, sodium bicarbonate, methylsulfonylmethane, vitamin C, xanthan gum, flavoring agent, or a mixture thereof. In some embodiments, the oral hygiene mouthwash composition may comprise water, xylitol, erythritol, inulin, hydroxyapatite, glycerin, sodium bicarbonate, methylsulfonylmethane, vitamin C, xanthan gum, and a flavoring agent. In some embodiments, the oral hygiene mouthwash composition may comprise water, xylitol, erythritol, inulin, hydroxyapatite, glycerin, sodium bicarbonate, methylsulfonylmethane, vitamin C, xanthan gum, sodium gluconate, vitamin D3, vitamin K2, flavoring agent, or a mixture thereof. In some embodiments, the oral hygiene mouthwash composition may comprise water, xylitol, erythritol, inulin, hydroxyapatite, glycerin, sodium bicarbonate, methylsulfonylmethane, vitamin C, xanthan gum, sodium gluconate, vitamin D3, vitamin K2, and a flavoring agent. In some embodiments, the oral hygiene mouthwash composition may comprise water, xylitol, erythritol, inulin, hydroxyapatite, glycerin, sodium bicarbonate, methylsulfonylmethane, vitamin C, xanthan gum, sodium gluconate, sodium fluoride, vitamin D3, vitamin K2, flavoring agent, or a mixture thereof. In some embodiments, the oral hygiene mouthwash composition may comprise water, xylitol, erythritol, inulin, hydroxyapatite, glycerin, sodium bicarbonate, methylsulfonylmethane, vitamin C, xanthan gum, sodium gluconate, sodium fluoride, vitamin D3, vitamin K2, and a flavoring agent.

In some embodiments, the oral hygiene mouth spray composition may comprise water, xylitol, erythritol, inulin, methylsulfonylmethane, glycerin, sodium bicarbonate, vitamin C, xanthan gum, flavoring agent, or a mixture thereof. In some embodiments, the oral hygiene mouth spray composition may comprise water, xylitol, erythritol, inulin, methylsulfonylmethane, glycerin, sodium bicarbonate, vitamin C, xanthan gum, and a flavoring agent. In some embodiments, the oral hygiene mouth spray composition may comprise water, xylitol, erythritol, inulin, methylsulfonylmethane, glycerin, sodium bicarbonate, vitamin C, xanthan gum, sodium gluconate, flavoring agent, or a mixture thereof. In some embodiments, the oral hygiene mouth spray composition may comprise water, xylitol, erythritol, inulin, methylsulfonylmethane, glycerin, sodium bicarbonate, vitamin C, xanthan gum, sodium gluconate, and a flavoring agent.

Devices

Devices comprising the oral hygiene composition are disclosed herein. In some embodiments, a device may include a flossing material and an oral hygiene composition described herein.

In some embodiments, the flossing material may be selected from polyester, rayon, viscose rayon, polytetrafluoroethylene (PTFE), nylon, Teflon, silk, and combinations thereof. In some embodiments, the flossing material has a thread count of, of about, of at least, or of at least about 500 dtex, 700 dtex, 900 dtex, 950 dtex, 1000 dtex, 1050 dtex, 1070 dtex, 1100 dtex, 1150 dtex, 1200 dtex, 1250 dtex, 1300 dtex, 1350 dtex, 1370 dtex, 1400 dtex, 1500 dtex, 1700 dtex or 2000 dtex, or any range of values therebetween. In some embodiments, the flossing material comprises the oral hygiene composition. In some embodiments, the oral hygiene composition is absorbed into the flossing material. In some embodiments, the flossing material is configured to expand due to mechanical friction. Examples of flossing materials include Riser® Expanding Floss.

In some embodiments, the oral hygiene device may further comprise hydroxyapatite, xylitol, erythritol, *stevia* leaf extract, vitamin D3, vitamin K2, or a mixture thereof. In some embodiments, the oral hygiene device may further comprise hydroxyapatite, xylitol, erythritol, *stevia* leaf extract, vitamin D3, and vitamin K2. In some embodiments, the oral hygiene device may further comprise hydroxyapatite, xylitol, erythritol, *stevia* leaf extract, vitamin D3, vitamin K2, limonene, linalool, or a mixture thereof. In some embodiments, the oral hygiene device may further comprise hydroxyapatite, xylitol, erythritol, *stevia* leaf extract, vitamin D3, vitamin K2, limonene, and linalool. In some embodiments, the device further includes aroma. In some embodiments, the device further includes a wax. In some embodiments, the flossing material further includes a wax. In some embodiments, the wax may include beeswax.

In some embodiments, the oral hygiene device comprises limonene of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.2 wt. %, 0.3 wt. %, 0.4 wt. %, 0.5 wt. %, 0.6 wt. 0.7 wt. %, 0.8 wt. %, 0.9 wt. %, 1 wt. %, 1.5 wt. %, 2 wt. %, 3 wt. %, 4 wt. % or 5 wt. %, or any range of values therebetween. For example, in some embodiments, the amount of limonene in the oral hygiene device is or is about in any one of the following ranges: 0.01-0.1 wt. %, 0.1-1 wt. %, 0.1-2 wt. %, 0.5-1.5 wt. %, 0.1-0.3 wt. % or 0.1-0.9 wt. % (based on total weight of the composition).

In some embodiments, the oral hygiene device comprises linalool of, of about, of at least, or at least about, 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.2 wt. %, 0.3 wt. %, 0.4 wt. %, 0.5 wt. %, 0.6 wt. 0.7 wt. %, 0.8 wt. %, 0.9 wt. %, or 1 wt. %, or any range of values therebetween. For example, in some embodiments, the amount of linalool in the oral hygiene device is or is about in any one of the following ranges: 0.01-0.09 wt. %, 0.1-1 wt. %, 0.01-1 wt. %, or 0.05-0.5 wt. % (based on total weight of the composition).

Methods of Treatment

The oral hygiene compositions and/or devices described here may be utilized to treat a subject. In some embodiments, the subject may be an adult and/or a child.

Some embodiments described herein generally relate to a method of treating or preventing bone growth deficiencies within a mouth or nose of the subject, harmful bacterial growth within the oral cavity, gingiva inflammation within the oral cavity, tooth decay within the oral cavity, tooth mineralization deficiencies, bone mineralization deficiencies, gum disease and/or halitosis (e.g., bad breath). In some embodiments, the oral hygiene compositions and/or devices described here may be utilized to promote beneficial bacterial growth within the oral cavity. In some embodiments, the oral hygiene compositions and/or devices described here may be utilized to whiten teeth, alkalize the pH of the mouth, reduce tooth and/or root sensitivity, and/or buffer teeth against acid erosion.

In some embodiments, the oral hygiene composition and/or device is administered to the oral cavity of a subject. In some embodiments, the oral hygiene composition and/or device is administered to the tooth of a subject. In some embodiments, the oral hygiene composition and/or device is administered between adjacent teeth of a subject. In some embodiments, the oral hygiene composition and/or device is administered to the gums of a subject.

Kits

Some embodiments described herein relate to a kit that can include an oral hygiene composition and/or device described herein. In some embodiments, the kit further comprises at least 1, 2, 3, 4 or five containers.

In some embodiments, the kit may include a remineralization agent, an anti-inflammatory agent, a prebiotic agent, an alkalizing agent, or a mixture thereof. For example, in some embodiments, the kit may include a remineralization agent, an anti-inflammatory agent, a prebiotic agent, and an alkalizing agent. In some embodiments, the kit may include a remineralization agent, an anti-inflammatory agent, and a prebiotic agent. In some embodiments, the kit may include an anti-inflammatory agent, a prebiotic agent, and an alkalizing agent. In some embodiments, the kit may include a remineralization agent and a prebiotic agent.

Examples

Varies oral hygiene compositions and devices have been prepare, utilizing the mixtures disclosed hereinabove. Some oral hygiene composition embodiments include toothpastes, mouthwashes, mouth sprays, and dental flosses. Example formulations of oral hygiene compositions are disclosed herein.

Example 1: Toothpaste Formulation

A toothpaste composition comprising:
19 wt. % water;
15 wt. % hydrated silica;
15 wt. % hydroxyapatite;
17 wt. % glycerin;
10 wt. % erythritol;
15 wt. % xylitol;
5 wt. % inulin;
1 wt. % methylsulfonylmethane;
1 wt. % calcium carbonate;
0.3 wt. % *Quillaja saponaria* extract;
0.05 wt. % *stevia* leaf extract;
0.5 wt. % dicalcium phosphate;
0.45 wt. % xanthan gum;
0.1 wt. % vitamin C;
<4 wt. % sodium gluconate;
0.05 wt. % cranberry seed oil;
0.0015 wt. % vitamin D3;
0.006 wt. % vitamin K2; and
0.2 wt. % flavoring agent.

Example 2: Toothpaste Formulation

A toothpaste composition comprising:
balance water;
15 wt. % hydrated silica;
5 wt. % hydroxyapatite;
20.5 wt. % glycerin;

10 wt. % erythritol;
15 wt. % xylitol;
5 wt. % inulin;
1 wt. % methylsulfonylmethane;
1 wt. % calcium carbonate;
0.3 wt. % *Quillaja saponaria* extract;
0.08 wt. % *stevia* leaf extract;
0.5 wt. % dicalcium phosphate;
0.35 wt. % xanthan gum;
0.1 wt. % vitamin C;
2 wt. % sodium gluconate;
0.05 wt. % cranberry seed oil;
0.0015 wt. % vitamin D3;
0.006 wt. % vitamin K2;
1 wt. % color; and
0.26 wt. % flavoring agent.

Example 3: Toothpaste Formulation

A toothpaste composition comprising:
20.8 wt. % water;
15 wt. % hydrated silica;
15 wt. % hydroxyapatite;
24 wt. % glycerin;
10 wt. % erythritol;
15 wt. % xylitol;
5 wt. % inulin;
1 wt. % methylsulfonylmethane;
0.3 wt. % *Quillaja saponaria* extract;
0.08 wt. % *stevia* leaf extract;
0.35 wt. % xanthan gum;
0.1 wt. % vitamin C;
2 wt. % sodium gluconate;
0.05 wt. % cranberry seed oil;
0.0015 wt. % vitamin D3;
0.006 wt. % vitamin K2;
0.24 wt. % sodium fluoride;
0.8 wt. % color; and
0.26 wt. % flavoring agent.

Example 4: Toothpaste Formulation

A toothpaste composition comprising:
balance water;
15 wt. % hydrated silica;
15 wt. % hydroxyapatite;
24 wt. % glycerin;
10 wt. % erythritol;
15 wt. % xylitol;
5 wt. % inulin;
1 wt. % methylsulfonylmethane;
0.3 wt. % *Quillaja saponaria* extract;
0.08 wt. % *stevia* leaf extract;
0.35 wt. % xanthan gum;
0.1 wt. % vitamin C;
2 wt. % sodium gluconate;
0.05 wt. % cranberry seed oil;
0.0015 wt. % vitamin D3;
0.006 wt. % vitamin K2;
1.1 wt. % sodium fluoride;
0.8 wt. % color; and
0.26 wt. % flavoring agent.

Example 5: Toothpaste Formulation

A toothpaste composition comprising:
balance water;
15 wt. % hydrated silica;
1-15 wt. % hydroxyapatite;
17 wt. % glycerin;
10 wt. % erythritol;
15 wt. % xylitol;
5 wt. % inulin;
1 wt. % methylsulfonylmethane;
1 wt. % calcium carbonate;
0.3 wt. % *Quillaja saponaria* extract;
0.05 wt. % *stevia* leaf extract;
0.5 wt. % dicalcium phosphate;
0.45 wt. % xanthan gum;
0.1 wt. % vitamin C;
<4 wt. % sodium gluconate;
0.05 wt. % cranberry seed oil;
0.0015 wt. % vitamin D3;
0.006 wt. % vitamin K2; and
0.2 wt. % flavoring agent.

Example 6: Toothpaste Formulation

A toothpaste composition comprising:
balance water;
15 wt. % hydrated silica;
1-15 wt. % hydroxyapatite;
20.5 wt. % glycerin;
10 wt. % erythritol;
15 wt. % xylitol;
5 wt. % inulin;
1 wt. % methylsulfonylmethane;
1 wt. % calcium carbonate;
0.3 wt. % *Quillaja saponaria* extract;
0.08 wt. % *stevia* leaf extract;
0.5 wt. % dicalcium phosphate;
0.35 wt. % xanthan gum;
0.1 wt. % vitamin C;
2 wt. % sodium gluconate;
0.05 wt. % cranberry seed oil;
0.0015 wt. % vitamin D3;
0.006 wt. % vitamin K2;
1 wt. % color; and
0.26 wt. % flavoring agent.

Example 7: Toothpaste Formulation

A toothpaste composition comprising:
balance water;
15 wt. % hydrated silica;
1-15 wt. % hydroxyapatite;
24 wt. % glycerin;
10 wt. % erythritol;
15 wt. % xylitol;
5 wt. % inulin;
1 wt. % methylsulfonylmethane;
0.3 wt. % *Quillaja saponaria* extract;
0.08 wt. % *stevia* leaf extract;
0.35 wt. % xanthan gum;
0.1 wt. % vitamin C;
2 wt. % sodium gluconate;
0.05 wt. % cranberry seed oil;
0.0015 wt. % vitamin D3;
0.006 wt. % vitamin K2;
0.24 wt. % sodium fluoride;
0.8 wt. % color; and
0.26 wt. % flavoring agent.

Example 8: Toothpaste Formulation

A toothpaste composition comprising:
balance water;

15 wt. % hydrated silica;
1-15 wt. % hydroxyapatite;
24 wt. % glycerin;
10 wt. % erythritol;
15 wt. % xylitol;
5 wt. % inulin;
1 wt. % methylsulfonylmethane;
0.3 wt. % *Quillaja saponaria* extract;
0.08 wt. % *stevia* leaf extract;
0.35 wt. % xanthan gum;
0.1 wt. % vitamin C;
2 wt. % sodium gluconate;
0.05 wt. % cranberry seed oil;
0.0015 wt. % vitamin D3;
0.006 wt. % vitamin K2;
1.1 wt. % sodium fluoride;
0.8 wt. % color; and
0.26 wt. % flavoring agent.

Example 9: Mouthwash Formulation

A mouthwash composition comprising:
66 wt. % water;
10 wt. % xylitol;
10 wt. % erythritol;
5 wt. % inulin;
5 wt. % hydroxyapatite;
2 wt. % glycerin;
1 wt. % sodium bicarbonate;
1 wt. % methylsulfonylmethane;
0.1 wt. % vitamin C;
<4 wt. % sodium gluconate;
0.08 wt. % xanthan gum; and
0.2 wt. % flavoring agent.

Example 10: Mouthwash Formulation

A mouthwash composition comprising:
63.2 wt. % water;
10 wt. % xylitol;
10 wt. % erythritol;
5 wt. % inulin;
5 wt. % hydroxyapatite;
2 wt. % glycerin;
1 wt. % sodium bicarbonate;
1 wt. % methylsulfonylmethane;
0.1 wt. % vitamin C;
2 wt. % sodium gluconate;
0.08 wt. % xanthan gum;
0.000025 wt. % vitamin D3;
0.0001 wt. % vitamin K2;
0.4 wt. % color; and
0.25 wt. % flavoring agent.

Example 11: Mouthwash Formulation

A mouthwash composition comprising:
63 wt. % water;
10 wt. % xylitol;
10 wt. % erythritol;
5 wt. % inulin;
5 wt. % hydroxyapatite;
2 wt. % glycerin;
1 wt. % sodium bicarbonate;
1 wt. % methylsulfonylmethane;
0.1 wt. % vitamin C;
2 wt. % sodium gluconate;
0.08 wt. % xanthan gum;
0.02 wt. % sodium fluoride;
0.000025 wt. % vitamin D3;
0.0001 wt. % vitamin K2;
0.6 wt. % color; and
0.25 wt. % flavoring agent.

Example 12: Mouthwash Formulation

A mouthwash composition comprising:
balance water;
10 wt. % xylitol;
10 wt. % erythritol;
5 wt. % inulin;
5 wt. % hydroxyapatite;
2 wt. % glycerin;
1 wt. % sodium bicarbonate;
1 wt. % methylsulfonylmethane;
0.1 wt. % vitamin C;
2 wt. % sodium gluconate;
0.08 wt. % xanthan gum;
0.05 wt. % sodium fluoride;
0.000025 wt. % vitamin D3;
0.0001 wt. % vitamin K2;
0.6 wt. % color; and
0.25 wt. % flavoring agent.

Example 13: Mouth Spray Formulation

A mouth spray composition comprising:
68 wt. % water;
15 wt. % xylitol;
15 wt. % erythritol;
5 wt. % inulin;
0.5 wt. % methylsulfonylmethane;
2 wt. % glycerin;
1 wt. % sodium bicarbonate;
<4 wt. % sodium gluconate;
0.1 wt. % vitamin C;
0.08 wt. % xanthan gum; and
0.2 wt. % flavoring agent.

Example 14: Mouth Spray Formulation

A mouth spray composition comprising:
69.1 wt. % water;
10 wt. % xylitol;
10 wt. % erythritol;
5 wt. % inulin;
0.5 wt. % methylsulfonylmethane;
2 wt. % glycerin;
1 wt. % sodium bicarbonate;
2 wt. % sodium gluconate;
0.1 wt. % vitamin C;
0.08 wt. % xanthan gum; and
0.2 wt. % flavoring agent.

Example 15: Dental Floss Device

A dental floss material comprising:
Riser® Expanding Floss;
3 wt. % hydroxyapatite;
2 wt. % xylitol;
1.5 wt. % erythritol; and
1.5 wt. % *stevia* leaf extract.

Example 16: Dental Floss Device

A dental floss material comprising:
Riser® Expanding Floss;

1-5 wt. % hydroxyapatite;
0.1-5 wt. % fluoride;
0.1-5 wt. % xylitol;
0.1-5 wt. % erythritol; and
0.1-5 wt. % *stevia* leaf extract.

Example 17: Dental Floss Device

A dental floss material comprising:
Riser® Expanding Floss;
1-5 wt. % hydroxyapatite;
0.1-5 wt. % fluoride;
0.1-5 wt. % xylitol;
0.1-5 wt. % erythritol;
0.1-5 wt. % *stevia* leaf extract;
0.1-1 wt. % vitamin D3; and
0.1-1 wt. % vitamin K2.

Example 18: Dental Floss Device

A dental floss material comprising:
Floss material;
75-88.5 wt. % beeswax;
10-25 wt. % aroma (e.g. vanilla, strawberry and/or chocolate);
1-5 wt. % hydroxyapatite;
0.1-1 wt. % xylitol;
0.1-1 wt. % erythritol;
0.1-1 wt. % *stevia* leaf extract;
0.1-1 wt. % vitamin D3; and
0.1-1 wt. % vitamin K2.

Example 19: Dental Floss Device

A dental floss material comprising:
Floss material;
75-88.3 wt. % beeswax;
10-25 wt. % aroma;
1-5 wt. % hydroxyapatite;
0.1-1 wt. % xylitol;
0.1-1 wt. % erythritol;
0.11 wt. % *stevia* leaf extract;
0.1-1 wt. % vitamin D3;
0.1-1 wt. % vitamin K2
0.1-1 wt. % limonene; and
0.1-1 wt. % linalool.

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

The headings provided herein, if any, are for convenience only and do not necessarily affect the scope or meaning of the devices and methods disclosed herein.

What is claimed is:

1. An oral hygiene composition, comprising at least the following ingredients:
a remineralization agent comprising hydroxyapatite, vitamin D3, and vitamin K2;
an anti-inflammatory agent comprising methylsulfonylmethane, vitamin C, and cranberry seed oil;
a prebiotic agent comprising inulin, xylitol, and erythritol; and
an alkalizing agent comprising sodium bicarbonate;
wherein the oral hygiene composition comprises:
1-20 wt. % hydroxyapatite;
0.00001-0.01 wt. % vitamin D3;
0.00001-0.012 wt. % vitamin K2;
0.05-3 wt. % methylsulfonylmethane;
0.05-0.2 wt. % vitamin C;
0.02-0.1 wt. % cranberry seed oil;
3-7 wt. % inulin;
5-20 wt. % xylitol;
5-10 wt. % erythritol; and
0.5-3.0 wt. % sodium bicarbonate.

2. The composition of claim 1, wherein the remineralization agent further comprises a compound selected from the group consisting of calcium carbonate, dicalcium phosphate, fluoride, and combinations thereof.

3. The composition of claim 1, wherein the oral hygiene composition comprises:
2-15 wt. % hydroxyapatite;
0.0001-0.005 wt. % vitamin D3; and
0.0001-0.01 wt. % vitamin K2.

4. The composition of claim 1, further comprising fluoride.

5. The composition of claim 4, wherein the oral hygiene composition comprises 0.01-1.5 wt. % fluoride.

6. The composition of claim 1, wherein the anti-inflammatory agent further comprises a compound or composition selected from the group consisting of sodium gluconate, and combinations thereof.

7. The composition of claim 1, wherein the oral hygiene composition comprises:
1-2 wt. % methylsulfonylmethane;
0.1-0.15 wt. % vitamin C; and
0.03-0.08 wt. % cranberry seed oil.

8. The composition of claim 1, wherein the prebiotic agent further comprises a compound or composition selected from the group consisting of cranberry seed oil, xanthan gum, *stevia* leaf extract, and combinations thereof.

9. The composition of claim 1, wherein the oral hygiene composition comprises:
4-6 wt. % inulin;
8-15 wt. % xylitol; and
6-8 wt. % erythritol.

10. The composition of claim 1, wherein the alkalizing agent further comprises a compound selected from the group consisting of xylitol, erythritol, and combinations thereof.

11. The composition of claim 1, wherein the oral hygiene composition comprises:
1-2.5 wt. % sodium bicarbonate;
8-15 wt. % xylitol; and
6-8 wt. % erythritol.

12. The composition of claim 1, wherein the composition further comprises a solvent.

13. The composition of claim 12, wherein the solvent comprises a compound selected from the group consisting of water, glycerin, and combinations thereof.

14. The composition of claim 12, wherein the oral hygiene composition comprises:
15-75 wt. % water; and
1-20 wt. % glycerin.

15. The composition of claim 1, wherein composition further comprises a cleaning agent.

16. The composition of claim 15, wherein the cleaning agent comprises a compound or composition selected from the group consisting of hydrated silica, *Quillaja saponaria* extract, and combinations thereof.

17. The composition of claim 15, wherein the oral hygiene composition comprises:
10-20 wt. % hydrated silica; and
0.1-2 wt. % *Quillaja saponaria* extract.

* * * * *